(12) United States Patent
Maruyama

(10) Patent No.: US 9,200,098 B2
(45) Date of Patent: Dec. 1, 2015

(54) RADIATION-SENSITIVE COMPOSITION AND COMPOUND

(75) Inventor: Ken Maruyama, Tokyo (JP)

(73) Assignee: JSR CORPORATION, Tokyo (JP)

( * ) Notice: Subject to any disclaimer, the term of this patent is extended or adjusted under 35 U.S.C. 154(b) by 555 days.

(21) Appl. No.: 13/415,754

(22) Filed: Mar. 8, 2012

(65) Prior Publication Data

US 2012/0164582 A1    Jun. 28, 2012

Related U.S. Application Data

(63) Continuation of application No. PCT/JP2010/065260, filed on Sep. 6, 2010.

(30) Foreign Application Priority Data

| Sep. 11, 2009 | (JP) | 2009-211069 |
| Mar. 15, 2010 | (JP) | 2010-058358 |
| Jul. 21, 2010 | (JP) | 2010-164305 |

(51) Int. Cl.

| G03F 7/004  | (2006.01) |
| C07C 309/12 | (2006.01) |
| C07C 381/12 | (2006.01) |
| C08F 20/10  | (2006.01) |
| C07C 307/06 | (2006.01) |
| C07C 309/07 | (2006.01) |
| C07C 309/17 | (2006.01) |
| C08F 20/28  | (2006.01) |
| C08F 20/54  | (2006.01) |
| G03F 7/039  | (2006.01) |

(52) U.S. Cl.
CPC .............. *C08F 20/10* (2013.01); *C07C 307/06* (2013.01); *C07C 309/07* (2013.01); *C07C 309/12* (2013.01); *C07C 309/17* (2013.01); *C07C 381/12* (2013.01); *C08F 20/28* (2013.01); *C08F 20/54* (2013.01); *G03F 7/0045* (2013.01); *G03F 7/0392* (2013.01); *G03F 7/0397* (2013.01); *C07C 2101/08* (2013.01); *C07C 2101/14* (2013.01); *C07C 2102/42* (2013.01); *C07C 2103/74* (2013.01)

(58) Field of Classification Search
CPC ... G03F 7/0045; G03F 7/0397; G03F 7/0392; C07C 309/12; C07C 309/07; C07C 309/17; C07C 381/12
USPC ........... 430/270.1, 921, 922, 905; 562/41, 42, 562/109, 110; 560/9, 11, 14
See application file for complete search history.

(56) References Cited

U.S. PATENT DOCUMENTS

| 4,491,628 A | 1/1985 | Ito et al. |
| 5,112,719 A | 5/1992 | Yamada et al. |
| 5,290,657 A | 3/1994 | Uetani et al. |
| 5,744,537 A | 4/1998 | Brunsvold et al. |
| 7,414,148 B2 * | 8/2008 | Fujiwara et al. ............. 562/100 |
| 2010/0021852 A1 | 1/2010 | Nishimura et al. |

FOREIGN PATENT DOCUMENTS

| EP | 0159428 B1 | 10/1985 |
| EP | 0555861 B1 | 8/1993 |
| JP | 59-045439 | 3/1984 |
| JP | 59-093448 | 5/1984 |
| JP | 01-289946 | 11/1989 |
| JP | 01-289947 | 11/1989 |
| JP | 02-2560 | 1/1990 |
| JP | 03-128959 | 5/1991 |
| JP | 03-158855 | 7/1991 |
| JP | 03-179353 | 8/1991 |
| JP | 03-191351 | 8/1991 |
| JP | 03-200251 | 9/1991 |

(Continued)

OTHER PUBLICATIONS

Perfluorooctyl Sulfonates, Proposed Significant New Use Rule; Extension of Comment Period, Federal Register, Nov. 21, 2000, p. 69889-69891, vol. 65, No. 225.
Jiro et al., Resist Surface Roughness Calculated using Theoretical Percolation Model, Journal of Photopolymer Science and Technology, 1998, p. 571, vol. 11.
Eishi Shiobara et al., Resist Edge Roughness with Reducing Pattern Size, Proc. SPIE 1998, p. 313, vol. 3333.
S.C. Palmateer et al., Line Edge Roughness in sub-0.18- µm Resist Patterns, Proc. SPIE 1998, p. 634, vol. 3333.

(Continued)

*Primary Examiner* — John Chu
(74) *Attorney, Agent, or Firm* — Oblon, McClelland, Maier & Neustadt, L.L.P.

(57) ABSTRACT

A radiation-sensitive composition includes a photoacid generator shown by a general formula (0-1a). Each of $R^0$ individually represents a substituted or unsubstituted organic group which includes a carbon atom, a hydrogen atom, and an oxygen atom, and which includes at least one ester bond, and $M^+$ represents a monovalent onium cation. A compound is shown by a general formula (0). R represents a substituted or unsubstituted organic group which includes a carbon atom, a hydrogen atom, and an oxygen atom, and which includes at least one ester bond, and $M^+$ represents a monovalent onium cation.

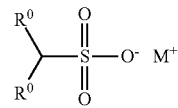

(0-1a)

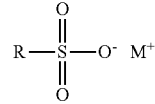

(0)

10 Claims, 1 Drawing Sheet

(56) References Cited

FOREIGN PATENT DOCUMENTS

| | | |
|---|---|---|
| JP | 03-200252 | 9/1991 |
| JP | 03-200253 | 9/1991 |
| JP | 03-200254 | 9/1991 |
| JP | 03-200255 | 9/1991 |
| JP | 03-259149 | 11/1991 |
| JP | 03-279958 | 12/1991 |
| JP | 03-279959 | 12/1991 |
| JP | 04-01650 | 1/1992 |
| JP | 04-01651 | 1/1992 |
| JP | 04-11260 | 1/1992 |
| JP | 04-12356 | 1/1992 |
| JP | 04-12357 | 1/1992 |
| JP | 04-271349 | 9/1992 |
| JP | 05-045869 | 2/1993 |
| JP | 05-158233 | 6/1993 |
| JP | 05-188598 | 7/1993 |
| JP | 05-224409 | 9/1993 |
| JP | 05-257275 | 10/1993 |
| JP | 05-297581 | 11/1993 |
| JP | 05-297583 | 11/1993 |
| JP | 05-303197 | 11/1993 |
| JP | 05-303200 | 11/1993 |
| JP | 05-341510 | 12/1993 |
| JP | 06-012452 | 1/1994 |
| JP | 10020468 A * | 1/1998 |
| JP | 10246943 A * | 9/1998 |
| JP | 2002-131897 | 5/2002 |
| JP | 2002-214774 | 7/2002 |
| JP | 2004-18394 | 1/2004 |
| JP | 2006-525265 | 11/2006 |
| JP | 2008-69146 | 3/2008 |
| JP | 2008-133262 | 6/2008 |
| JP | 2008249851 A | 10/2008 |
| JP | 2008268931 A | 11/2008 |
| JP | 2009-222920 | 10/2009 |
| JP | 2010-155824 | 7/2010 |
| WO | WO 2008/047678 | 4/2008 |
| WO | WO 2009/019793 | 2/2009 |

OTHER PUBLICATIONS

Hideo Namatsu et al., Three-dimensional siloxane resist for the formation of nanopatterns with minimum linewidth fluctuations, J. Vac. Sci. Technol. B 16(1), 1998, p. 69.

J.V. Crivello, Cationic Polymerization-Iodonium and Sulfonium Salt Photoinitiators, Advances in Polymer Science, 1984, p. 1-48, vol. 62.

International Search Report for corresponding International Application No. PCT/JP2010/065260, Oct. 5, 2010.

Masanao Era et al., Preparation of highly oriented poly (p-phenyleneviny lene) thin film by using Langmuir-Blodgett technique, Chemistry Letters, 1988, (7), p. 1097-1100.

Written Opinion with International Preliminary Report for corresponding International Application No. PCT/JP2010/065260, Oct. 5, 2010.

Japanese Office Action for related Japanese Application No. 2011-530831, dated Jun. 24, 2014, with English-language translation, 8 pages.

* cited by examiner

RADIATION-SENSITIVE COMPOSITION AND COMPOUND

CROSS-REFERENCE TO RELATED APPLICATIONS

The present application is a continuation application of International Application No. PCT/JP2010/065260, filed Sep. 6, 2010, which claims priority to Japanese Patent Application No. 2009-211069, filed Sep. 11, 2009, to Japanese Patent Application No. 2010-058358, filed Mar. 15, 2010 and to Japanese Patent Application No. 2010-164305, filed Jul. 21, 2010. The contents of these applications are incorporated herein by reference in their entirety.

BACKGROUND OF THE INVENTION

1. Field of the Invention

The invention relates to a radiation-sensitive composition and a compound.

2. Discussion of the Background

When deep ultraviolet rays (e.g., KrF excimer laser light or ArF excimer laser light) or the like are applied to a chemically-amplified radiation-sensitive resin composition, an acid is generated in the exposed area, and a difference in solubility rate in a developer occurs between the exposed area and the unexposed area due to chemical reactions catalyzed by the generated acid. A resist pattern is formed on a substrate by utilizing the difference in solubility rate (see Japanese Patent Application Publication (KOKAI) No. 59-45439 and Perfluorooctyl Sulfonates; Proposed Significant New Use Rule).

A photoacid generator included in the chemically-amplified radiation-sensitive resin composition is required to exhibit excellent transparency to radiation and have a high quantum yield when generating an acid. An acid generated by the photoacid generator is required to have sufficient acidity, a sufficiently high boiling point, and an appropriate diffusion distance (hereinafter may be referred to as "diffusion length") within the resist film, for example.

When using an ionic photoacid generator, the structure of the anion moiety is important in order to obtain sufficient acidity, a sufficiently high boiling point, and an appropriate diffusion length.

For example, a photoacid generator having a trifluoromethanesulfonyl structure generates an acid having sufficient acidity, and sufficiently increases the resolution of the photoresist. However, an acid generated by such a photoacid generator has a low boiling point and an inappropriate diffusion length. Specifically, sufficient resolution may not be obtained due to a long acid diffusion length.

A photoacid generator having a sulfonyl structure bonded to a large organic group (e.g., 10-camphorsulfonyl structure) generates an acid having a sufficiently high boiling point and an appropriate diffusion length (i.e., a sufficiently short diffusion length). However, the photoacid generator having a camphorsulfonyl structure may not be sufficiently dissolved in a solvent generally used for a radiation-sensitive resin composition due to poor solubility.

When precisely controlling the line width (e.g., when the device design dimensions are equal to or less than sub-half micrometers), it is important for a chemically-amplified resist to exhibit an excellent resolution and provide excellent surface flatness. When using a chemically-amplified resist that provides poor surface flatness, elevations and depressions (hereinafter may be referred to as "nano edge roughness") formed on the surface of the resist film may be transferred to a substrate when transferring the resist pattern to the substrate by etching or the like, so that the dimensional accuracy of the pattern may deteriorate. This may impair the electrical properties of the resulting device (see J. Photopolym. Sci. Tech., p. 571 (1998), Proc. SPIE, Vol. 3333, p. 313, Proc. SPIE, Vol. 3333, p. 634, and J. Vac. Sci. Technol. B16 (1), p. 69 (1998), for example).

SUMMARY OF THE INVENTION

According to one aspect of the present invention, a radiation-sensitive composition includes a photoacid generator shown by a general formula (0-1a).

Each of $R^0$ individually represents a substituted or unsubstituted organic group which includes a carbon atom, a hydrogen atom, and an oxygen atom, and which includes at least one ester bond, and $M^+$ represents a monovalent onium cation.

According to another aspect of the present invention, a compound is shown by a general formula (0).

R represents a substituted or unsubstituted organic group which includes a carbon atom, a hydrogen atom, and an oxygen atom, and which includes at least one ester bond, and $M^+$ represents a monovalent onium cation.

According to further aspect of the present invention, a compound is shown by a general formula (1).

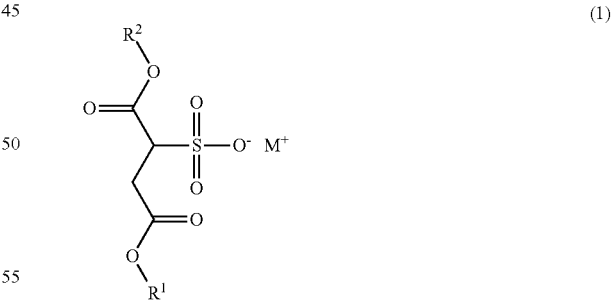

Each of $R^1$ and $R^2$ individually represents (a1) a substituted or unsubstituted linear or branched monovalent hydrocarbon group having 1 to 30 carbon atoms, (a2) the hydrocarbon group as defined in (a1) which further includes at least one of an ester bond, an amide bond, a urethane bond, and a sulfide bond, (a3) a substituted or unsubstituted cyclic or cyclic structure-containing monovalent hydrocarbon group having 3 to 30 carbon atoms, (a4) the hydrocarbon group as defined in (a3) which further includes at least one of an ester bond, an amide bond, a urethane bond, and a sulfide bond, (a5) a substituted or unsubstituted aryl group having 6 to 30 carbon atoms, or (a6) a substituted or unsubstituted cyclic organic group having 4 to 30 carbon atoms and optionally having a monovalent heteroatom. M+ represents a monovalent onium cation. The monovalent onium cation represented by M+ is a sulfonium cation shown by a general formula (2) or an iodonium cation shown by a general formula (3).

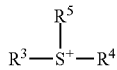  (2)

Each of $R^3$, $R^4$, and $R^5$ individually represents a substituted or unsubstituted linear or branched alkyl group having 1 to 10 carbon atoms or a substituted or unsubstituted aryl group having 6 to 18 carbon atoms, or two of $R^3$, $R^4$, and $R^5$ bond to each other to form a cyclic structure together with the sulfur atom in the general formula (2), and the remainder of $R^3$, $R^4$, and $R^5$ represents a substituted or unsubstituted linear or branched alkyl group having 1 to 10 carbon atoms or a substituted or unsubstituted aryl group having 6 to 18 carbon atoms.

$R^6$—$I^+$—$R^7$  (3)

Each of $R^6$ and $R^7$ individually represents a substituted or unsubstituted linear or branched alkyl group having 1 to 10 carbon atoms or a substituted or unsubstituted aryl group having 6 to 18 carbon atoms, or bond to each other to form a cyclic structure with the iodine atom in the general formula (3).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DESCRIPTION OF THE EMBODIMENTS

Figure 1:
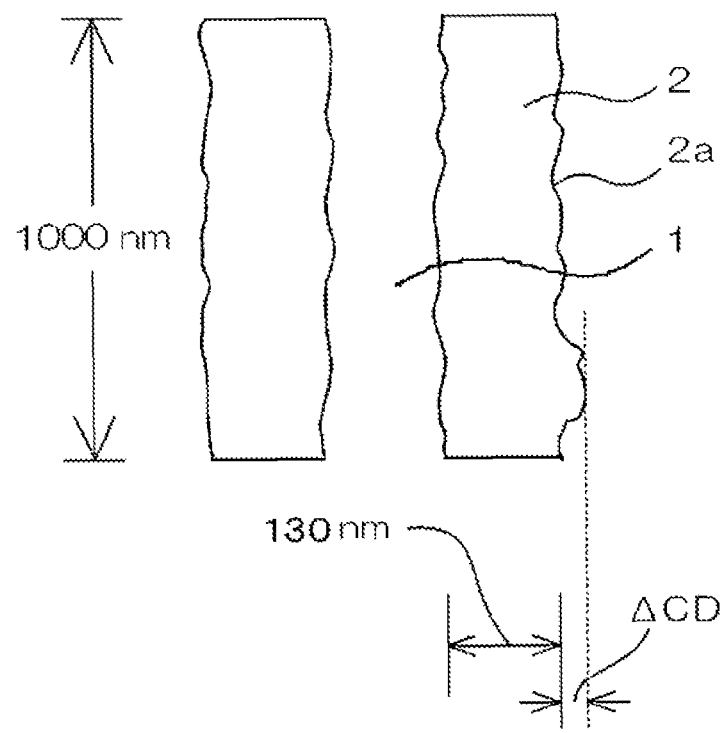
FIG. 1 is a plan view schematically showing a line pattern.

Specifically, an embodiment of the present invention provides the following.

[1] A radiation-sensitive composition including (A) a photoacid generator shown by a general formula (0),

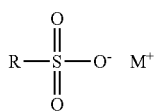  (0)

wherein R represents a substituted or unsubstituted organic group that includes a carbon atom, a hydrogen atom, and an oxygen atom, and includes at least one ester bond, and M+ represents a monovalent onium cation.

[2] The radiation-sensitive composition according to [1], wherein the organic group represented by R in the general formula (1) includes two or more ester bonds.

[3] The radiation-sensitive composition according to [1] or [2], wherein the photoacid generator is shown by a general formula (0-1a),

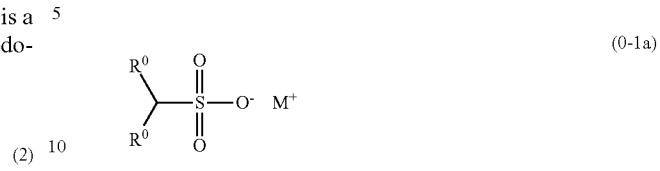  (0-1a)

wherein $R^0$ individually represent a substituted or unsubstituted organic group that includes a carbon atom, a hydrogen atom, and an oxygen atom, and includes at least one ester bond, and M+ represents a monovalent onium cation.

[4] The radiation-sensitive composition according to any one of [1] to [3], wherein the photoacid generator is shown by a general formula (1),

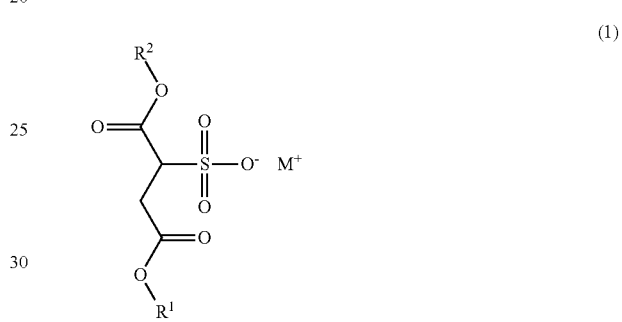  (1)

wherein $R^1$ and $R^2$ individually represent (a1) a substituted or unsubstituted linear or branched monovalent hydrocarbon group having 1 to 30 carbon atoms, (a2) the hydrocarbon group as defined in (a1) that further includes a linking group selected from an ester bond, an amide bond, a urethane bond, and a sulfide bond, (a3) a substituted or unsubstituted cyclic or cyclic structure-containing monovalent hydrocarbon group having 3 to 30 carbon atoms, (a4) the hydrocarbon group as defined in (a3) that further includes a linking group selected from an ester bond, an amide bond, a urethane bond, and a sulfide bond, (a5) a substituted or unsubstituted aryl group having 6 to 30 carbon atoms, or (a6) a substituted or unsubstituted cyclic organic group having 4 to 30 carbon atoms that may include a monovalent heteroatom, and M+ represents a monovalent onium cation.

[5] The radiation-sensitive composition according to any one of [1] to [4], wherein the monovalent onium cation represented by M+ is a sulfonium cation shown by a general formula (2) or an iodonium cation shown by a general formula (3),

  (2)

wherein $R^3$, $R^4$, and $R^5$ individually represent a substituted or unsubstituted linear or branched alkyl group having 1 to 10 carbon atoms or a substituted or unsubstituted aryl group having 6 to 18 carbon atoms, or two of $R^3$, $R^4$, and $R^5$ bond to each other to form a cyclic structure together with a sulfur atom in the general formula (2), and the remainder of $R^3$, $R^4$, and $R^5$ represents a substituted or unsubstituted linear or branched alkyl group having 1 to 10 carbon atoms or a substituted or unsubstituted aryl group having 6 to 18 carbon atoms,

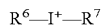 (3)

wherein $R^6$ and $R^7$ individually represent a substituted or unsubstituted linear or branched alkyl group having 1 to 10 carbon atoms or a substituted or unsubstituted aryl group having 6 to 18 carbon atoms, or bond to each other to form a cyclic structure with an iodine atom in the general formula (3).

[6] The radiation-sensitive composition according to any one of [1] to [5], further including a resin that includes at least one repeating unit among repeating units shown by general formulas (b-1) to (b-5),

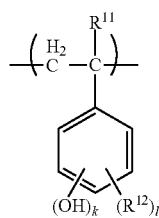 (b-1)

wherein $R^{11}$ represents a hydrogen atom or a methyl group, $R^{12}$ represents a linear or branched alkyl group having 1 to 12 carbon atoms or a linear or branched alkoxy group having 1 to 12 carbon atoms, k is an integer from 0 to 3, and l is an integer from 0 to 3, provided that k+l≤5 is satisfied,

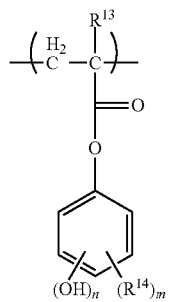 (b-2)

wherein $R^{13}$ represents a hydrogen atom or a methyl group, $R^{14}$ represents a linear or branched alkyl group having 1 to 12 carbon atoms or a linear or branched alkoxy group having 1 to 12 carbon atoms, m is an integer from 0 to 3, and n is an integer from 0 to 3, provided that m+n≤5 is satisfied,

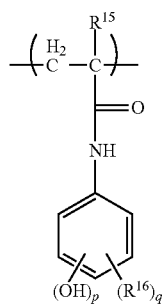 (b-3)

wherein $R^{15}$ represents a hydrogen atom or a methyl group, $R^{16}$ represents a linear or branched alkyl group having 1 to 12 carbon atoms or a linear or branched alkoxy group having 1 to 12 carbon atoms, p is an integer from 0 to 3, and q is an integer from 0 to 3, provided that p+q≤5 is satisfied,

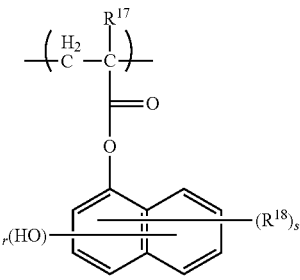 (b-4)

wherein $R^{17}$ represents a hydrogen atom or a methyl group, $R^{18}$ represents a linear or branched alkyl group having 1 to 12 carbon atoms or a linear or branched alkoxy group having 1 to 12 carbon atoms, r is an integer from 0 to 3, and s is an integer from 0 to 3,

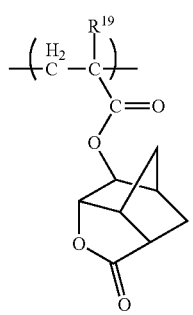 (b-5)

wherein $R^{19}$ represents a hydrogen atom or a methyl group.

[7] The radiation-sensitive composition according to any one of [1] to [6], further including at least one compound selected from ethylene glycol monoalkyl ether acetates and propylene glycol monoalkyl ether acetates as a solvent in an amount of 70 to 100 parts by mass based on 100 parts by mass of the solvent in total.

[8] A compound shown by a general formula (0),

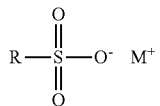 (0)

wherein R represents a substituted or unsubstituted organic group that includes a carbon atom, a hydrogen atom, and an oxygen atom, and includes at least one ester bond, and $M^+$ represents a monovalent onium cation.

[9] A compound shown by a general formula (1),

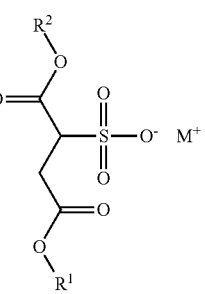 (1)

wherein R¹ and R² individually represent (a1) a substituted or unsubstituted linear or branched monovalent hydrocarbon group having 1 to 30 carbon atoms, (a2) the hydrocarbon group as defined in (a1) that further includes a linking group selected from an ester bond, an amide bond, a urethane bond, and a sulfide bond, (a3) a substituted or unsubstituted cyclic or cyclic structure-containing monovalent hydrocarbon group having 3 to 30 carbon atoms, (a4) the hydrocarbon group as defined in (a3) that further includes a linking group selected from an ester bond, an amide bond, a urethane bond, and a sulfide bond, (a5) a substituted or unsubstituted aryl group having 6 to 30 carbon atoms, or (a6) a substituted or unsubstituted cyclic organic group having 4 to 30 carbon atoms that may include a monovalent heteroatom, and M⁺ represents a monovalent onium cation.

The radiation-sensitive composition according to the embodiment of the invention may produce a chemically-amplified positive-tone resist film that effectively responds to (extreme) deep ultraviolet rays (e.g., KrF excimer laser light, ArF excimer laser light, or EUV), X-rays such as synchrotron radiation, or electron beams, shows only a small degree of nano edge roughness, exhibits excellent sensitivity and resolution, and stably and accurately produces a fine pattern.

The novel compound according to the embodiment of the invention exhibits high solubility in a solvent, and may suitably be used as the photoacid generator included in the radiation-sensitive composition according to the embodiment of the invention.

Exemplary embodiments will now be described with reference to the accompanying drawings, wherein like reference numerals designate corresponding or identical elements throughout the various drawings. Note that the invention is not limited to the following exemplary embodiments. It should be understood that various modifications, improvements, and the like may be made of the following exemplary embodiments without departing from the scope of the invention based on common knowledge of a person skilled in the art. The term "(meth)acrylate" used herein refers to "acrylate" or "methacrylate".

[1] Radiation-Sensitive Composition

A radiation-sensitive composition according to one embodiment of the invention includes (A) a specific photoacid generator.

[1-1] Photoacid Generator (A)

The photoacid generator (A) (hereinafter may be referred to as "acid generator (A)") is a compound shown by the following general formula (0). The acid generator (A) exhibits high solubility in a solvent. A radiation-sensitive composition that includes the acid generator (A) can form a resist film that produces an excellent resist pattern. The acid generator (A) rarely volatilizes during a photolithographic process due to a high boiling point, and generates an acid that exhibits a short acid diffusion length within a resist film. Specifically, the acid generator (A) generates an acid that exhibits a moderate acid diffusion length.

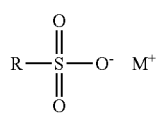

(0)

wherein R represents a substituted or unsubstituted organic group that includes a carbon atom, a hydrogen atom, and an oxygen atom, and includes at least one ester bond, and M⁺ represents a monovalent onium cation.

R in the general formula (0) represents an organic group that includes a carbon atom, a hydrogen atom, and an oxygen atom, and includes an ester bond.

The number of ester bonds included in the organic group may be one, or may be two or more. The number of ester bonds included in the organic group is preferably 1 to 4.

One or more hydrogen atoms of the organic group may be substituted with a substituent. Specific examples of the substituent include a hydroxyl group, a thiol group, an alkyl group, a heteroatom (e.g., halogen atom (e.g., fluorine atom, chlorine atom, bromine atom, and iodine atom), oxygen atom, nitrogen atom, sulfur atom, phosphorus atom, and silicon atom), and the like.

The acid generator (A) shown by the general formula (0) is preferably a compound shown by the following general formula (0-1a).

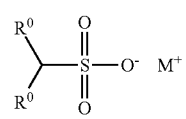

(0-1a)

wherein R⁰ individually represent a substituted or unsubstituted organic group that includes a carbon atom, a hydrogen atom, and an oxygen atom, and includes at least one ester bond, and M⁺ represents a monovalent onium cation.

Examples of the organic group represented by R⁰ in the general formula (0-1a) include groups shown by the following formulas (0-1a-1) to (0-1a-4). It is preferable that at least one of R⁰ represent any of the groups shown by the formulas (0-1a-2) to (0-1a-4).

(0-1a-1)

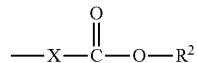

(0-1a-2)

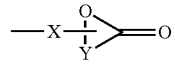

(0-1a-3)

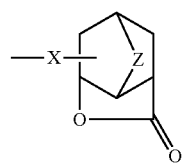

(0-1a-4)

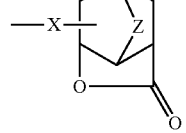

wherein R^a represents (a1) a substituted or unsubstituted linear or branched monovalent hydrocarbon group having 1 to 30 carbon atoms, (a1-1) the hydrocarbon group as defined in (a1) that further includes a linking group selected from an amide bond, a urethane bond, and a sulfide bond, (a3) a substituted or unsubstituted cyclic or cyclic structure-containing monovalent hydrocarbon group having 3 to 30 carbon atoms, (a3-1) the hydrocarbon group as defined in (a3) that further includes a linking group selected from an amide bond, a urethane bond, and a sulfide bond, (a5) a substituted or unsubstituted aryl group having 6 to 30 carbon atoms, or (a6) a substituted or unsubstituted cyclic organic group having 4 to 30 carbon atoms that may include a monovalent heteroatom.

X in the general formula (0-1a-2) represents a single bond, a methylene group, an alkylene group having 2 to 10 carbon atoms, an alicyclic hydrocarbon group having 3 to 30 carbon atoms, or an aryl group having 6 to 30 carbon atoms.

$R^2$ in the general formula (0-1a-2) represents (a1) a substituted or unsubstituted linear or branched monovalent hydrocarbon group having 1 to 30 carbon atoms, (a2) the hydrocarbon group as defined in (a1) that further includes a linking group selected from an ester bond, an amide bond, a urethane bond, and a sulfide bond, (a3) a substituted or unsubstituted cyclic or cyclic structure-containing monovalent hydrocarbon group having 3 to 30 carbon atoms, (a4) the hydrocarbon group as defined in (a3) that further includes a linking group selected from an ester bond, an amide bond, a urethane bond, and a sulfide bond, (a5) a substituted or unsubstituted aryl group having 6 to 30 carbon atoms, or (a6) a substituted or unsubstituted cyclic organic group having 4 to 30 carbon atoms that may include a monovalent heteroatom.

The groups ((a1) to (a6)) represented by $R^a$ in the general formula (0-1a-1) and $R^2$ in the general formula (0-1a-2) are the same as groups (a1) to (a6) described later in connection with $R^1$ and $R^2$ in the general formula (1).

Examples of the hydrocarbon group ((a1-1)) that further includes a linking group selected from n amide bond, a urethane bond, and a sulfide bond include a group obtained by substituting a carbon-carbon bond included in the substituted or unsubstituted linear or branched monovalent hydrocarbon group having 1 to 30 carbon atoms as defined in (a1) with at least one linking group selected from an amide bond, a urethane bond, and a sulfide bond.

Examples of the hydrocarbon group ((a3-1)) that further includes a linking group selected from an amide bond, a urethane bond, and a sulfide bond include a group obtained by substituting a carbon-carbon bond included in the substituted or unsubstituted cyclic or cyclic structure-containing monovalent hydrocarbon group having 3 to 30 carbon atoms as defined in (a3) with at least one linking group selected from an amide bond, a urethane bond, and a sulfide bond.

X in the general formula (0-1a-3) is the same as defined for X in the general formula (0-1a-2). Y in the general formula (0-1a-3) represents a methylene group or an alkylene group having 2 to 6 carbon atoms.

X in the general formula (0-1a-4) is the same as defined for X in the general formula (0-1a-2). Z in the general formula (0-1a-4) represents a methylene group, an ethylene group, an oxygen atom, or a sulfur atom.

The acid generator (A) shown by the general formula (0) is particularly preferably a compound shown by the following general formula (1).

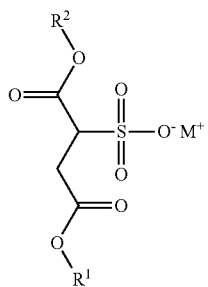

(1)

wherein $R^1$ and $R^2$ individually represent (a1) a substituted or unsubstituted linear or branched monovalent hydrocarbon group having 1 to 30 carbon atoms, (a2) the hydrocarbon group as defined in (a1) that further includes a linking group selected from an ester bond, an amide bond, a urethane bond, and a sulfide bond, (a3) a substituted or unsubstituted cyclic or cyclic structure-containing monovalent hydrocarbon group having 3 to 30 carbon atoms, (a4) the hydrocarbon group as defined in (a3) that further includes a linking group selected from an ester bond, an amide bond, a urethane bond, and a sulfide bond, (a5) a substituted or unsubstituted aryl group having 6 to 30 carbon atoms, or (a6) a substituted or unsubstituted cyclic organic group having 4 to 30 carbon atoms that may include a monovalent heteroatom, and $M^+$ represents a monovalent onium cation.

Examples of the unsubstituted linear or branched monovalent hydrocarbon group having 1 to 30 carbon atoms represented by $R^1$ and $R^2$ in the general formula (1) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, an n-nonyl group, an n-decyl group, a 2-ethylhexyl group, an n-dodecyl group, and the like.

Examples of a substituent that may substitute the linear or branched monovalent hydrocarbon group having 1 to 30 carbon atoms include a halogen atom (e.g., fluorine atom, chlorine atom, bromine atom, or iodine atom), a hydroxyl group, a thiol group, an aryl group, an alkenyl group, an organic group (e.g., alkyl group) that includes a heteroatom (e.g., halogen atom, oxygen atom, nitrogen atom, sulfur atom, phosphorus atom, or silicon atom), and the like. The linear or branched monovalent hydrocarbon group having 1 to 30 carbon atoms may be substituted with a keto group (i.e., two hydrogen atoms bonded to a single carbon of the hydrocarbon group are substituted with an oxygen atom). The number of substituents is not particularly limited.

Examples of the substituted linear or branched monovalent hydrocarbon group having 1 to 30 carbon atoms include a benzyl group, a methoxymethyl group, a methylthiomethyl group, an ethoxymethyl group, a phenoxymethyl group, a methoxycarbonylmethyl group, an ethoxycarbonylmethyl group, an acetylmethyl group, a fluoromethyl group, a trifluoromethyl group, a 2,2,2-trifluoroethyl group, a chloromethyl group, a trichloromethyl group, a 2-fluoropropyl group, a trifluoroacetylmethyl group, a trichloroacetylmethyl group, a pentafluorobenzoylmethyl group, an aminomethyl group, a cyclohexylaminomethyl group, a diphenylphosphinomethyl group, a trimethylsilylmethyl group, a 2-phenylethyl group, a 3-phenylpropyl group, a 2-aminoethyl group, a hydroxymethyl group, a hydroxyethyl group, a hydroxycarbonylmethyl group, and the like.

Examples of the hydrocarbon group ((a2)) that further includes a linking group selected from an ester bond, an amide bond, a urethane bond, and a sulfide bond include a group obtained by substituting a carbon-carbon bond included in the substituted or unsubstituted linear or branched monovalent hydrocarbon group having 1 to 30 carbon atoms with at least one linking group selected from an ester bond, an amide bond, a urethane bond, and a sulfide bond.

Examples of the substituted or unsubstituted cyclic or cyclic structure-containing monovalent hydrocarbon group having 3 to 30 carbon atoms represented by $R^1$ and $R^2$ in the general formula (1) include a cyclopropyl group, a cyclobutyl group, a cyclopentyl group, a cyclohexyl group, a bornyl group, a norbornyl group, an adamantyl group, a pinanyl group, a thujyl group, a caryl group, a camphanyl group, a cyclopropylmethyl group, a cyclobutylmethyl group, a cyclopentylmethyl group, a cyclohexylmethyl group, a bornylmethyl group, a norbornylmethyl group, an adamantylmethyl group, and the like.

Examples of a substituent that may substitute the cyclic or cyclic structure-containing monovalent hydrocarbon group having 3 to 30 carbon atoms include those mentioned above in connection with the linear or branched monovalent hydrocarbon group having 1 to 30 carbon atoms.

Examples of the substituted cyclic or cyclic structure-containing monovalent hydrocarbon group having 3 to 30 carbon atoms include a 4-fluorocyclohexyl group, a 4-hydroxycyclohexyl group, a 4-methoxycyclohexyl group, a 4-methoxycarbonylcyclohexyl group, a 3-hydroxy-1-adamantyl group, a 3-methoxycarbonyl-1-adamantyl group, a 3-hydroxycarbonyl-1-adamantyl group, a 3-hydroxymethyl-1-adamantanemethyl group, and the like.

Examples of the hydrocarbon group ((a4)) that further includes a linking group selected from an ester bond, an amide bond, a urethane bond, and a sulfide bond include a group obtained by substituting a carbon-carbon bond included in the substituted or unsubstituted cyclic or cyclic structure-containing monovalent hydrocarbon group having 3 to 30 carbon atoms with at least one linking group selected from an ester bond, an amide bond, a urethane bond, and a sulfide bond.

Examples of the aryl group having 6 to 30 carbon atoms represented by $R^1$ and $R^2$ in the general formula (1) include a phenyl group, a 1-naphthyl group, a 2-naphthyl group, a 1-anthryl group, a 1-phenanthryl group, and the like.

Examples of a substituent that may substitute the aryl group having 6 to 30 carbon atoms include a halogen atom (e.g., fluorine atom, chlorine atom, bromine atom, and iodine atom), a hydroxyl group, a thiol group, an alkyl group, an organic group that includes a heteroatom (e.g., halogen atom, oxygen atom, nitrogen atom, sulfur atom, phosphorus atom, or silicon atom), and the like.

Examples of the substituted aryl group having 6 to 30 carbon atoms include an o-hydroxyphenyl group, an m-hydroxyphenyl group, a p-hydroxyphenyl group, a 3,5-bis(hydroxy)phenyl group, an o-tolyl group, an m-tolyl group, a p-tolyl group, a p-methoxyphenyl group, a mesityl group, an o-cumenyl group, a 2,3-xylyl group, an o-fluorophenyl group, an m-fluorophenyl group, a p-fluorophenyl group, an o-trifluoromethylphenyl group, an m-trifluoromethylphenyl group, a p-trifluoromethylphenyl group, a 3,5-bis(trifluoromethyl)phenyl group, a p-bromophenyl group, a p-chlorophenyl group, a p-iodophenyl group, and the like.

Examples of the cyclic monovalent organic group having 4 to 30 carbon atoms that may include a heteroatom represented by $R^1$ and $R^2$ in the general formula (1) include a furyl group, a thienyl group, a pyranyl group, a pyrrolyl group, a thianthrenyl group, a pyrazolyl group, an isothiazolyl group, an isooxazolyl group, a pyrazinyl group, a pyrimidinyl group, a pyridazinyl group, a group derived from a monocyclic or polycyclic lactone, and the like.

Examples of the monocyclic or polycyclic lactone include γ-butyrolactone, γ-valerolactone, angelica lactone, γ-hexylactone, γ-heptalactone, γ-octalactone, γ-nonalactone, 3-methyl-4-octanolide (whisky lactone), γ-decalactone, γ-undecalactone, γ-dodecalactone, γ-jasmolactone (7-decenolactone), δ-hexylactone, 4,6,6(4,4,6)-trimethyltetrahydropyran-2-one, δ-octalactone, δ-nonalactone, δ-decalactone, δ-2-decenolactone, δ-undecalactone, δ-dodecalactone, δ-tridecalactone, δ-tetradecalactone, lactoscatone, ε-decalactone, ε-dodecalactone, cyclohexyllactone, jasmine lactone, cis-jasmone lactone, methyl-γ-decalactone, lactones shown by the following formulas (R-1) and (R-2) (note that a dotted line indicates a bonding site), and the like.

(R-1)

(R-2)

Examples of a substituent that may substitute the cyclic organic group that may include a heteroatom include those mentioned above in connection with the linear or branched monovalent hydrocarbon group having 1 to 30 carbon atoms.

Examples of the substituted cyclic monovalent organic group having 4 to 30 carbon atoms that may include a heteroatom include a 2-bromofuryl group, 3-methoxythienyl group, and the like.

Specific examples of the structures shown by the general formulas (0) and (1) include the structures shown by the following formulas (0-1) to (0-59) and (1-1) to (1-21), and the like. Note that $M^+$ (monovalent onium cation) in each formula is described below.

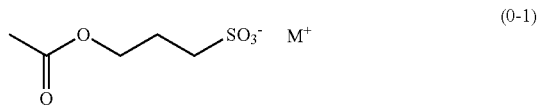

(0-1)

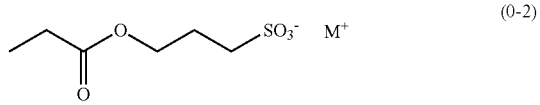

(0-2)

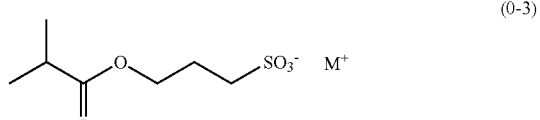

(0-3)

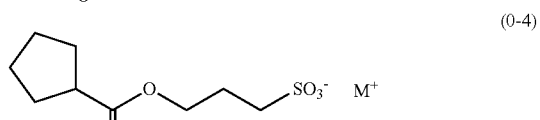

(0-4)

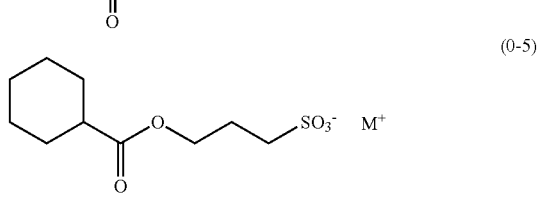

(0-5)

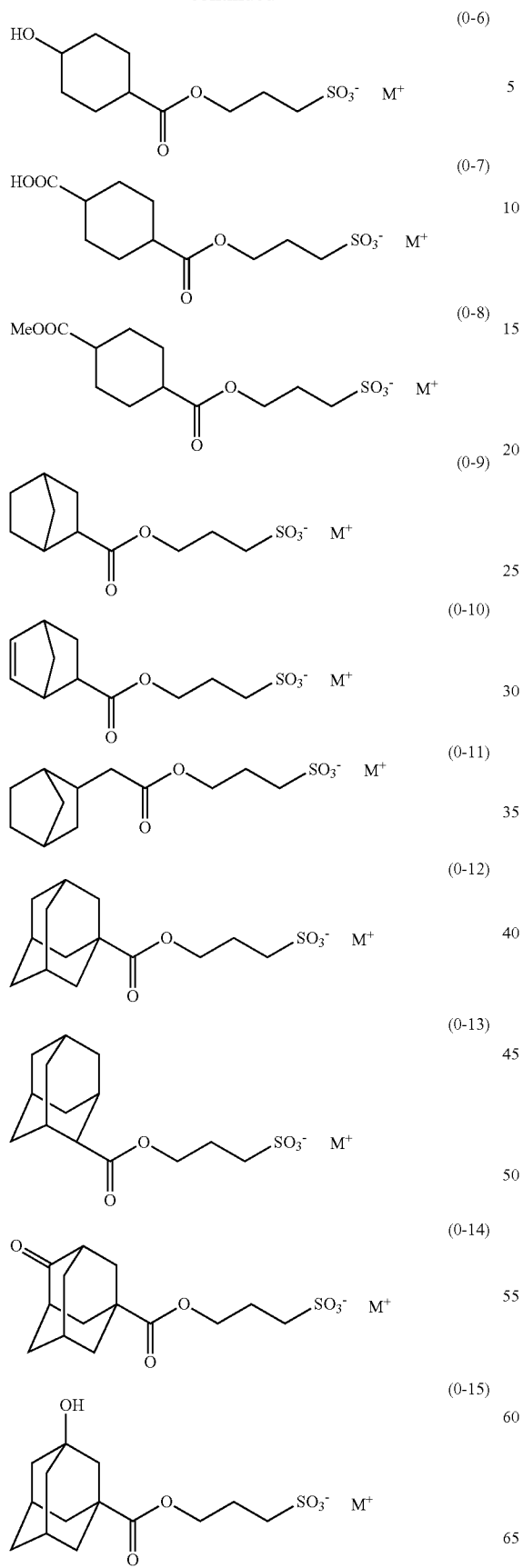
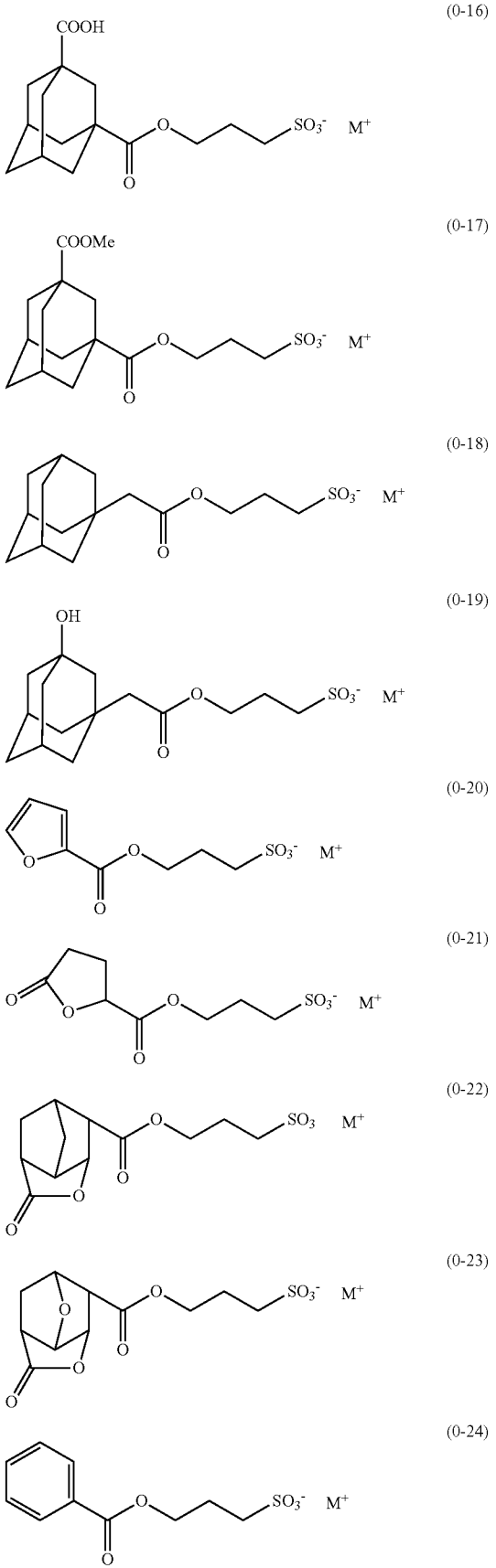

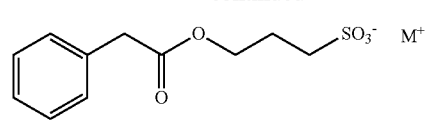 (0-25)
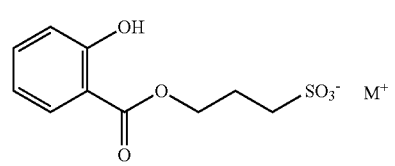 (0-26)
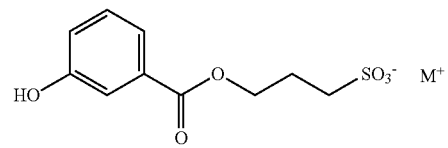 (0-27)
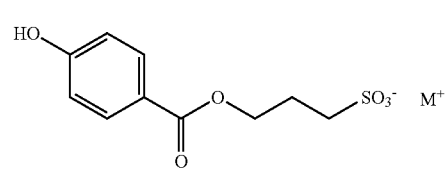 (0-28)
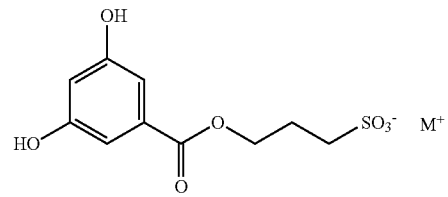 (0-29)
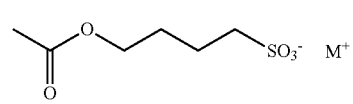 (0-30)
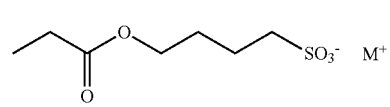 (0-31)
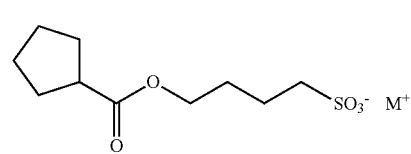 (0-32)
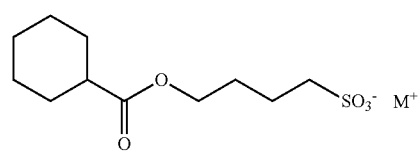 (0-33)
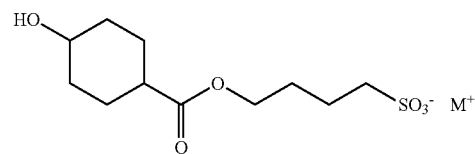 (0-34)
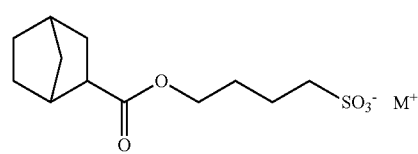 (0-35)
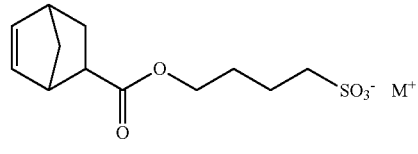 (0-36)
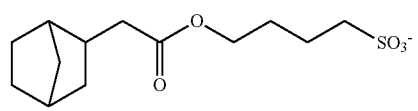 (0-37)
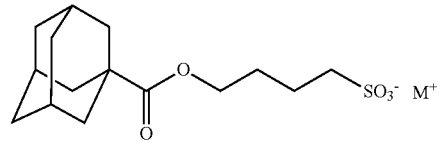 (0-38)
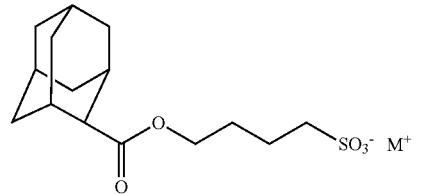 (0-39)
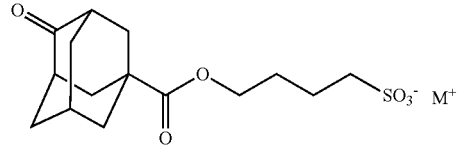 (0-40)
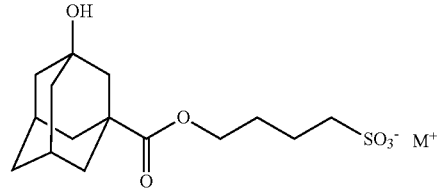 (0-41)
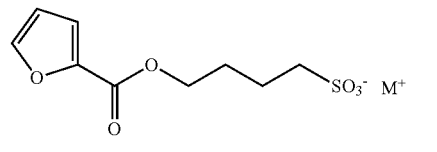 (0-42)
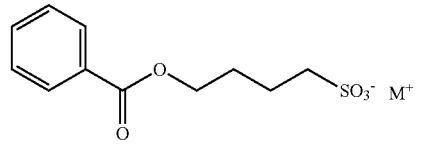 (0-43)
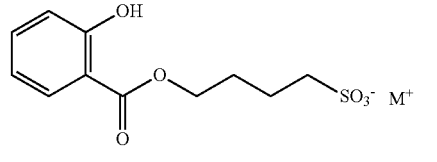 (0-44)
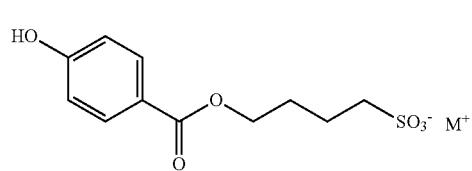 (0-45)

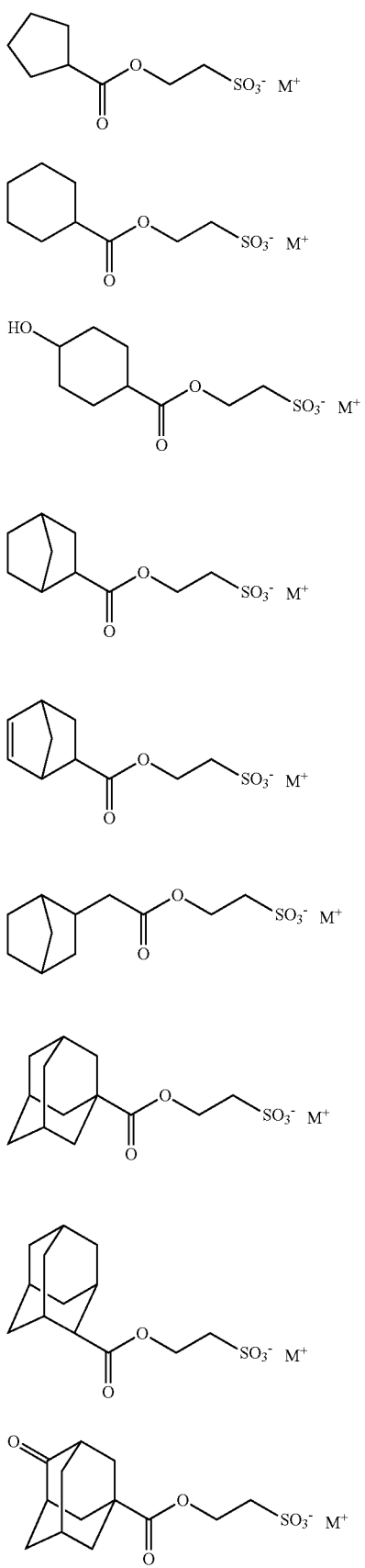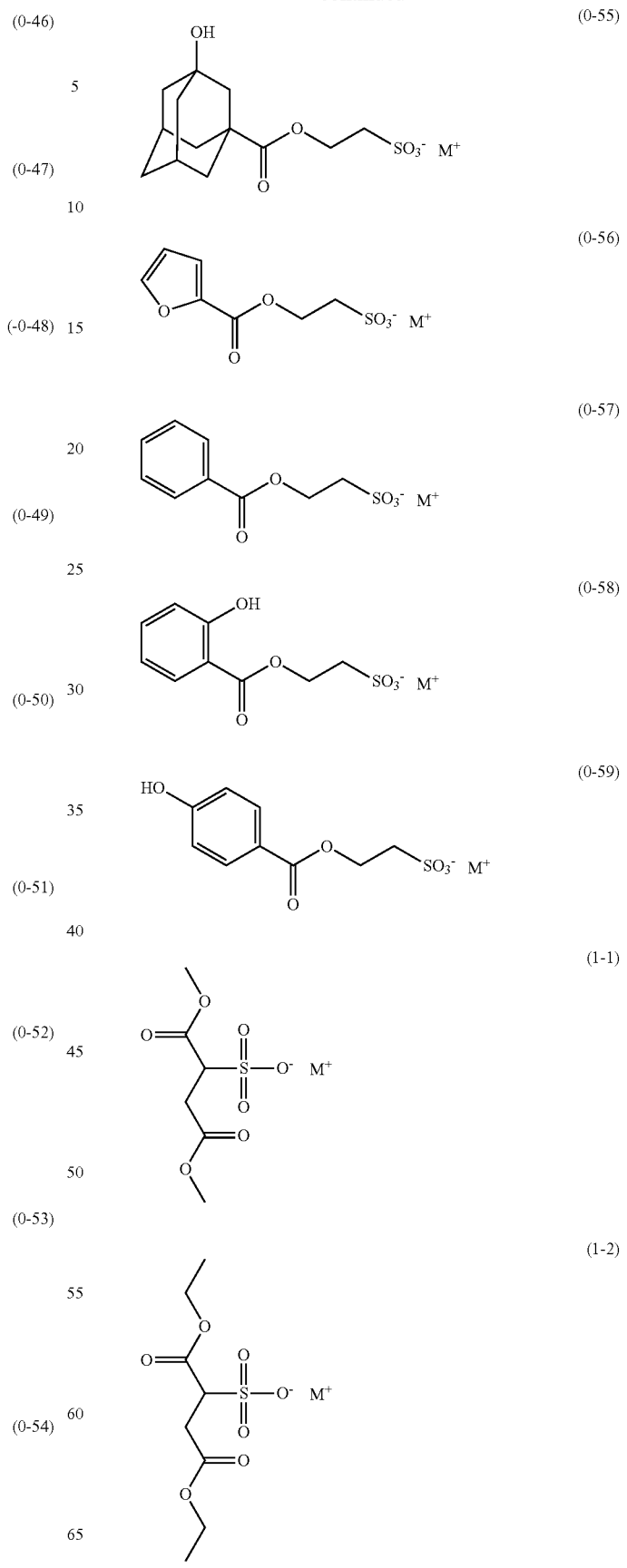

(1-3)
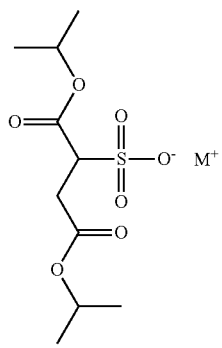
(1-4)
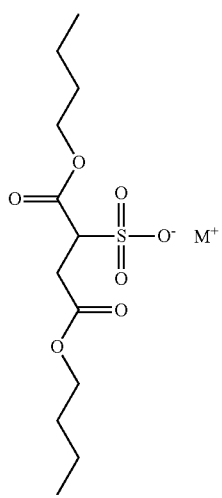
(1-5)
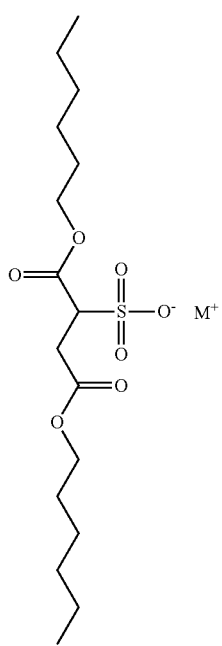
(1-6)
(1-7)
(1-8)
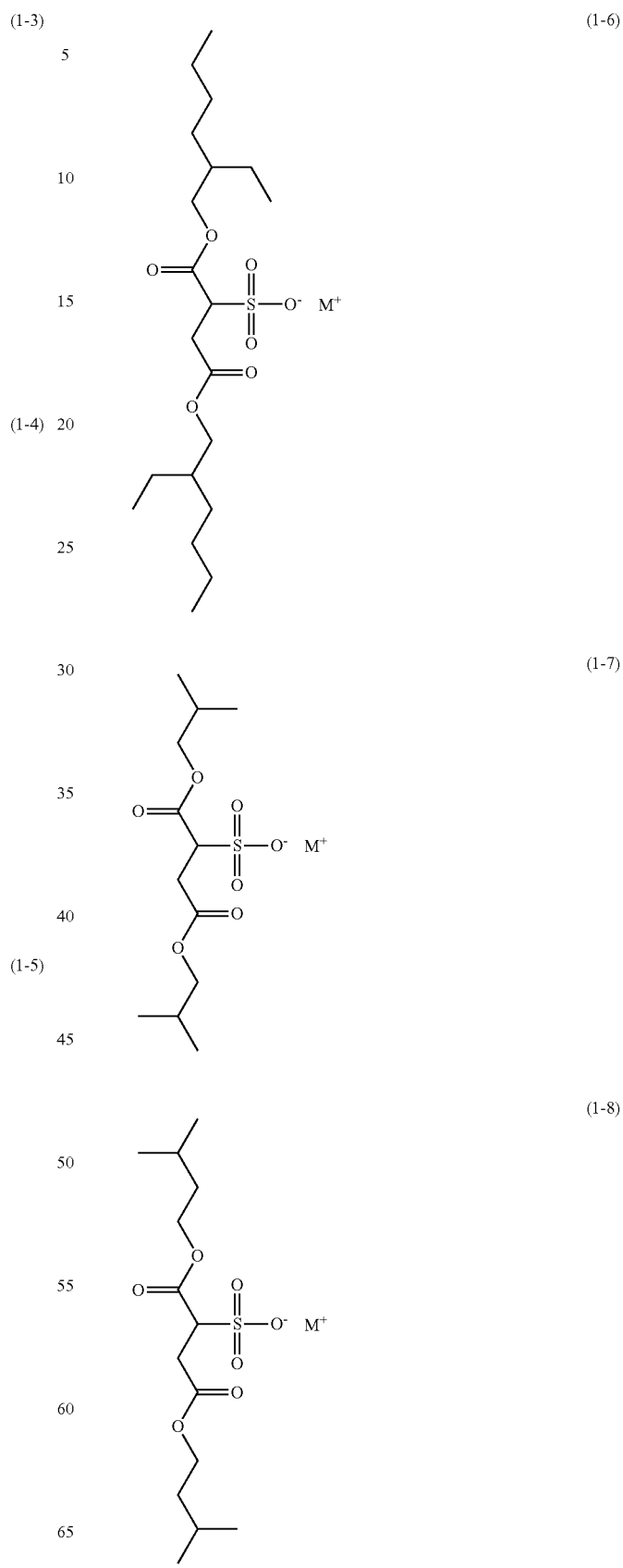

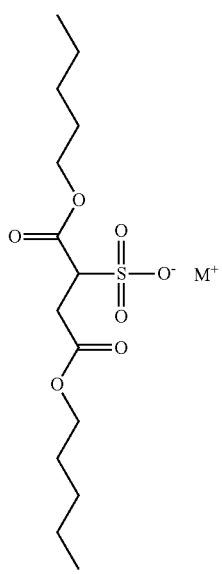
(1-9)
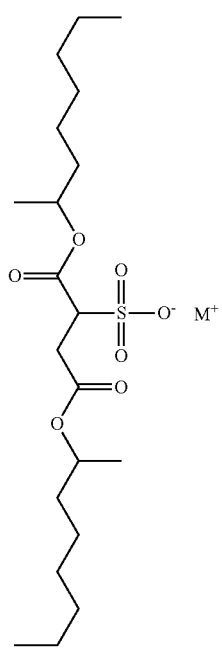
(1-10)
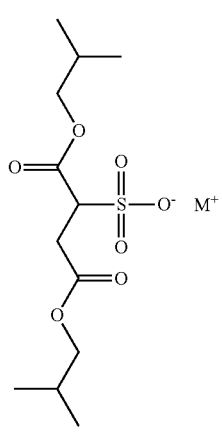
(1-11)
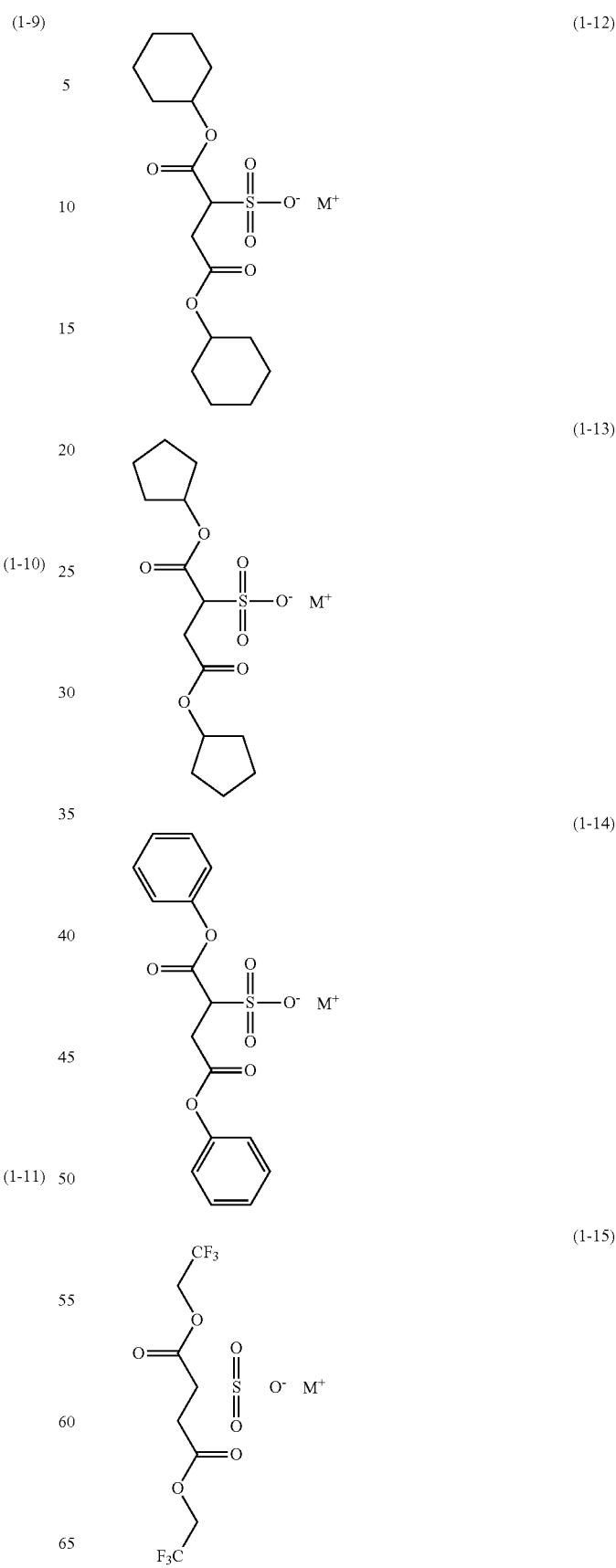

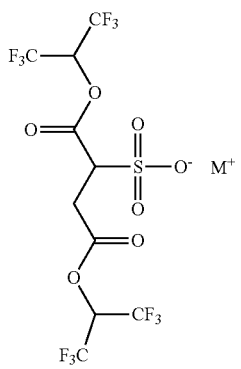
(1-16)
(1-17)
(1-18)
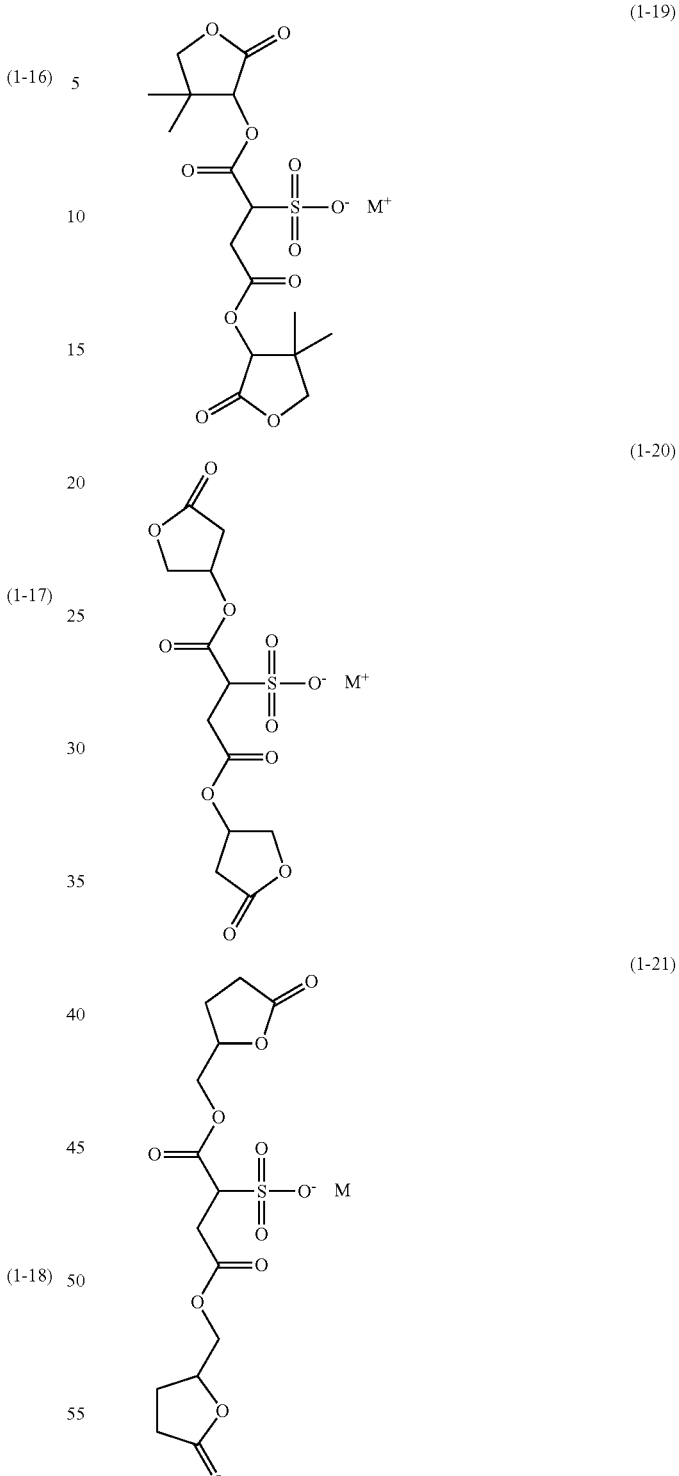
(1-19)
(1-20)
(1-21)
Examples of the monovalent onium cation represented by $M^+$ in the general formulas (0) and (1) and the formulas (0-1) to (0-59) and (1-1) to (1-21) include onium cations of O, S, Se, N, P, As, Sb, Cl, Br, I, and the like. Among these, onium cations of S and I are preferable.
Specific examples of the sulfonium cation (onium cation of S) include a sulfonium cation shown by the following general formula (2). Specific examples of the iodonium cation (onium cation of I) include an iodonium cation shown by the following general formula (3).

$$R^3-\overset{R^5}{\underset{|}{S^+}}-R^4 \quad (2)$$

wherein $R^3$, $R^4$, and $R^5$ individually represent a substituted or unsubstituted linear or branched alkyl group having 1 to 10 carbon atoms or a substituted or unsubstituted aryl group having 6 to 18 carbon atoms, or two of $R^3$, $R^4$, and $R^5$ bond to each other to form a cyclic structure together with a sulfur atom in the general formula (2), and the remainder of $R^3$, $R^4$, and $R^5$ represents a substituted or unsubstituted linear or branched alkyl group having 1 to 10 carbon atoms or a substituted or unsubstituted aryl group having 6 to 18 carbon atoms.

$$R^6-I^+-R^7 \quad (3)$$

wherein $R^6$ and $R^7$ individually represent a substituted or unsubstituted linear or branched alkyl group having 1 to 10 carbon atoms or a substituted or unsubstituted aryl group having 6 to 18 carbon atoms, or bond to each other to form a cyclic structure with an iodine atom in the general formula (3).

Examples of the unsubstituted linear or branched alkyl group having 1 to 10 carbon atoms represented by $R^3$ to $R^5$ in the general formula (2) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, an n-nonyl group, an n-decyl group, a 2-ethylhexyl group, and the like. The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the unsubstituted aryl group having 6 to 18 carbon atoms represented by $R^3$ to $R^5$ in the general formula (2) include a phenyl group, a 1-naphthyl group, a 2-naphthyl group, a 1-anthryl group, a 1-phenanthryl group, and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

An onium cation shown by the following general formula (2-1) or (2-2) is preferable as the onium cation shown by the general formula (2).

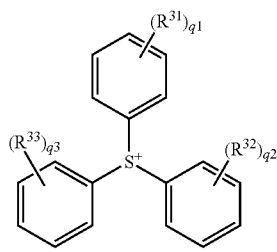

(2-1)

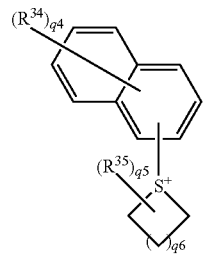

(2-2)

wherein $R^{31}$ to $R^{33}$ individually represent a hydrogen atom, a substituted or unsubstituted linear or branched alkyl group having 1 to 12 carbon atoms, a substituted or unsubstituted aryl group having 6 to 12 carbon atoms, an $-OSO_2-R^{38}$ group, or an $-SO_2-R^{39}$ group, or two or more of $R^{31}$ to $R^{33}$ bond to form a ring, provided that a plurality of $R^{31}$, a plurality of $R^{32}$, and a plurality of $R^{33}$ may respectively be either the same or different when a plurality of $R^{31}$, a plurality of $R^{32}$, and/or a plurality of $R^{33}$ are present, $R^{38}$ and $R^{39}$ individually represent a substituted or unsubstituted linear or branched alkyl group having 1 to 12 carbon atoms, a substituted or unsubstituted alicyclic hydrocarbon group having 5 to 25 carbon atoms, or a substituted or unsubstituted aryl group having 6 to 12 carbon atoms, q1 to q3 are individually integers from 0 to 5, $R^{34}$ represents a hydrogen atom, a substituted or unsubstituted linear or branched alkyl group having 1 to 8 carbon atoms, or a substituted or unsubstituted aryl group having 6 to 8 carbon atoms, or two or more $R^{34}$ bond to each other to form a ring, provided that a plurality of $R^{34}$ may be either the same or different when a plurality of $R^{34}$ are present, $R^{35}$ represents a hydrogen atom, a substituted or unsubstituted linear or branched alkyl group having 1 to 7 carbon atoms, or a substituted or unsubstituted aryl group having 6 to 7 carbon atoms, or two or more $R^{35}$ bond to each other to form a ring, provided that a plurality of $R^{35}$ may be either the same or different when a plurality of $R^{35}$ are present, q4 is an integer from 0 to 7, q5 is an integer from 0 to 6, and q6 is an integer from 0 to 3.

Examples of the unsubstituted linear or branched alkyl group having 1 to 12 carbon atoms represented by $R^{31}$ to $R^{33}$ in the general formula (2-1) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, an n-nonyl group, an n-decyl group, a 2-ethylhexyl group, and the like. The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the aryl group having 6 to 12 carbon atoms represented by $R^{31}$ to $R^{33}$ include a phenyl group, a naphthyl group, and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

Examples of the unsubstituted linear or branched alkyl group having 1 to 12 carbon atoms represented by $R^{38}$ and $R^{39}$ in the general formula (2-1) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, an n-nonyl group, an n-decyl group, a 2-ethylhexyl group, and the like. The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the alicyclic hydrocarbon group having 5 to 25 carbon atoms represented by $R^{38}$ and $R^{39}$ include a cyclopentyl group, a cyclohexyl group, a cyclooctyl group, an adamantyl group, a norbornyl group, and the like. The alicyclic hydrocarbon group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

Examples of the unsubstituted aryl group having 6 to 12 carbon atoms represented by $R^{38}$ and $R^{39}$ include a phenyl group, a naphthyl group, and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

Examples of the unsubstituted linear or branched alkyl group having 1 to 8 carbon atoms represented by $R^{34}$ in the general formula (2-2) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, a 2-ethylhexyl group, and the like. The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the unsubstituted aryl group having 6 to 8 carbon atoms represented by $R^{34}$ include a phenyl group and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

Examples of the unsubstituted linear or branched alkyl group having 1 to 7 carbon atoms represented by $R^{35}$ in the general formula (2-2) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, and the like. The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the unsubstituted aryl group having 6 to 7 carbon atoms represented by $R^{35}$ include a phenyl group and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

The sulfonium cations shown by the following formulas (i-1) to (i-13) are preferable as the sulfonium cation shown by the general formula (2-1) or (2-2).

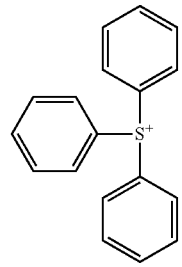

(i-1)

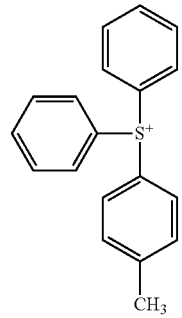

(i-2)

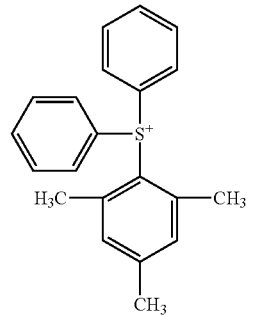

(i-3)

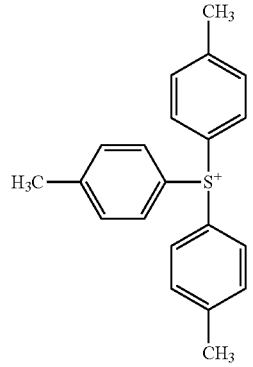

(i-4)

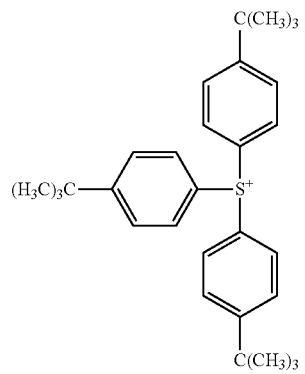

(i-5)

(i-5) 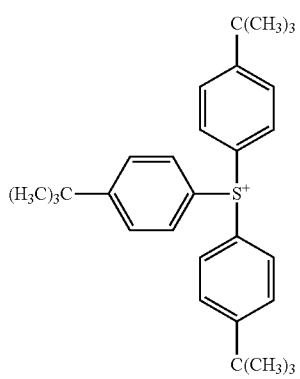

(i-6) 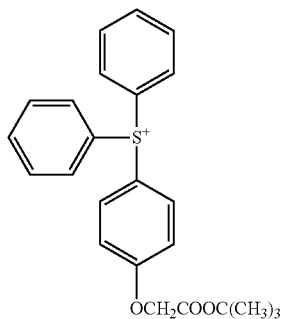

(i-7) 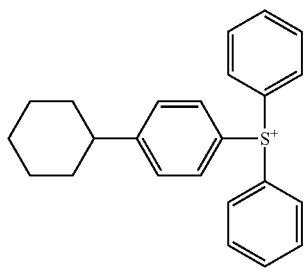

(i-8) 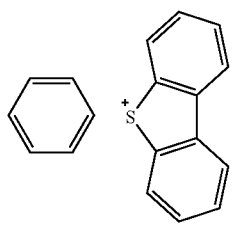

(i-9) 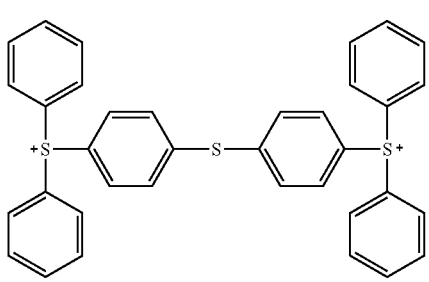

(i-10) 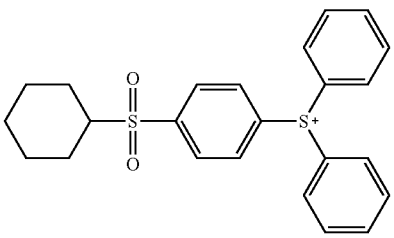

(i-11) 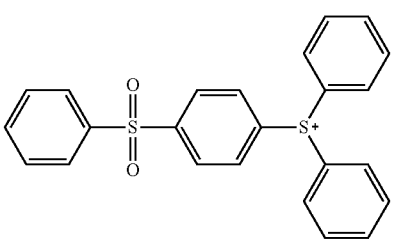

(i-12) 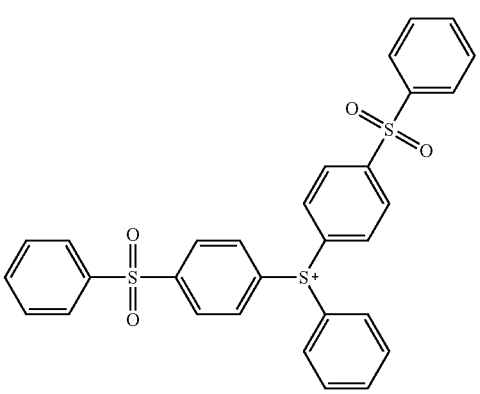

(i-13) 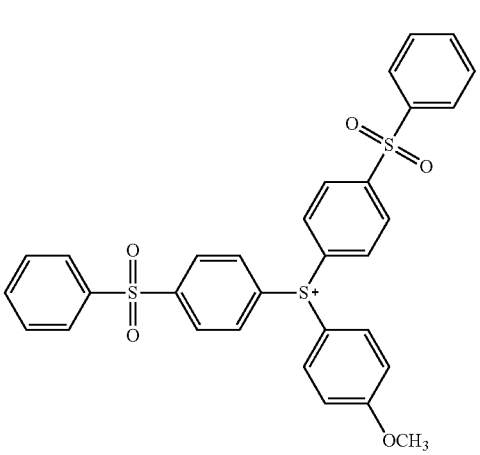

Examples of the unsubstituted linear or branched alkyl group having 1 to 10 carbon atoms represented by $R^6$ and $R^7$ in the general formula (3) include a methyl group, an ethyl group, an n-propyl group, an i-propyl group, an n-butyl group, a t-butyl group, an n-pentyl group, an i-pentyl group, an n-hexyl group, an i-hexyl group, an n-heptyl group, an n-octyl group, an i-octyl group, an n-nonyl group, an n-decyl group, a 2-ethylhexyl group, and the like. The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the aryl group having 6 to 18 carbon atoms represented by $R^6$ and $R^7$ in the general formula (3) include a phenyl group, a 1-naphthyl group, a 2-naphthyl group, a 1-anthryl group, a 1-phenanthryl group, and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

An onium cation shown by the following general formula (3-1) is preferable as the onium cation shown by the general formula (3).

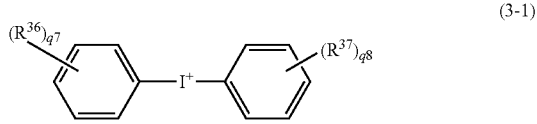

(3-1)

wherein $R^{36}$ and $R^{37}$ individually represent a hydrogen atom, a substituted or unsubstituted linear or branched alkyl group having 1 to 12 carbon atoms, or a substituted or unsubstituted aryl group having 6 to 12 carbon atoms, or two or more of $R^{36}$ and $R^{37}$ bond to form a ring, provided that a plurality of $R^{36}$ and/or a plurality of $R^{37}$ may respectively be either the same or different when a plurality of $R^{36}$ and/or a plurality of $R^{37}$ are present, and q7 and q8 are individually integers from 0 to 5.

Examples of the unsubstituted linear or branched alkyl group having 1 to 12 carbon atoms represented by $R^{36}$ and $R^{37}$ in the general formula (3-1) include a methyl group, an ethyl group, an n-propyl group, an i-propyl group, an n-butyl group, a 2-methylpropyl group, a 1-methylpropyl group, a t-butyl group, and the like. The alkyl group may be substituted with a halogen atom (e.g., fluorine atom, chlorine atom, bromine atom, or iodine atom), a hydroxyl group, a thiol group, an organic group that includes a heteroatom (e.g., halogen atom, oxygen atom, nitrogen atom, sulfur atom, phosphorus atom, or silicon atom), or the like.

Examples of the aryl group having 6 to 12 carbon atoms represented by $R^{36}$ and $R^{37}$ include a phenyl group, a naphthyl group, and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

The iodonium cations shown by the following formulas (ii-1) to (ii-3) are preferable as the iodonium cation shown by the general formula (3-1).

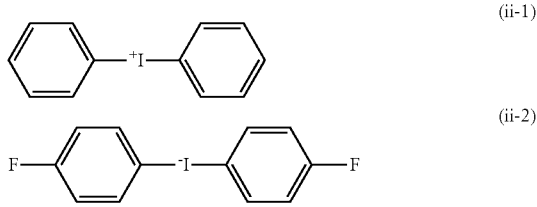

(ii-1)

(ii-2)

(ii-3)

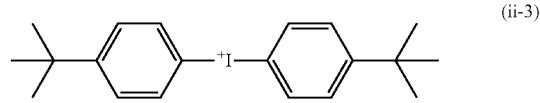

The sulfonium cations shown by the formulas (i-1) and (i-6) to (i-13) and the iodonium cations shown by the formulas (ii-1) and (ii-2) are particularly preferable as the monovalent onium cation.

The monovalent onium cation represented by $M^+$ included in the acid generator (A) may be produced by the method described in Advances in Polymer Science, vol. 62, pp. 1-48 (1984), for example.

The acid generator (A) included in the radiation-sensitive composition according to one embodiment of the invention generates an acid due to dissociation of the monovalent onium cation ($M^+$) upon exposure or heating. Specifically, the acid generator (A) generates a sulfonic acid shown by the following general formula (0a), and preferably generates a sulfonic acid shown by the following general formula (1a).

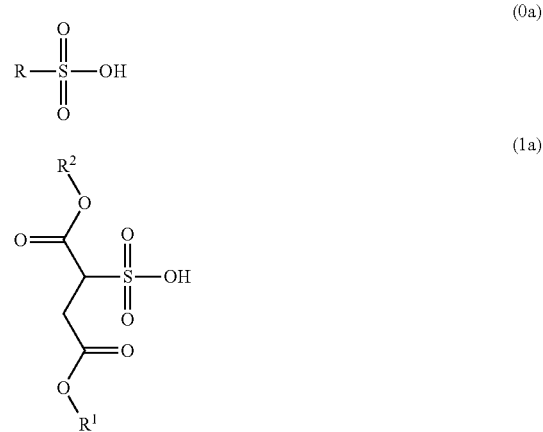

(0a)

(1a)

R in the general formula (0a) is the same as defined for R in the general formula (0). The description given above in connection with R in the general formula (0) may be applied to R in the general formula (0a). $R^1$ and $R^2$ in the general formula (1a) are the same as defined for $R^1$ and $R^2$ in the general formula (1). The description given above in connection with $R^1$ and $R^2$ in the general formula (1) may be applied to $R^1$ and $R^2$ in the general formula (1a).

The acid generator (A) may be synthesized by an arbitrary method. For example, the acid generator (A) may be synthesized by reacting a compound shown by the following general formula (X1) or (X2) with a halide of the desired onium cation ($M^+$) (e.g., $M^+Br^-$) in an aqueous solution (see the following reaction formulas).

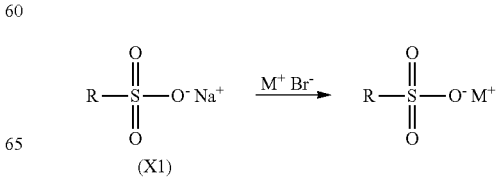

(X1)

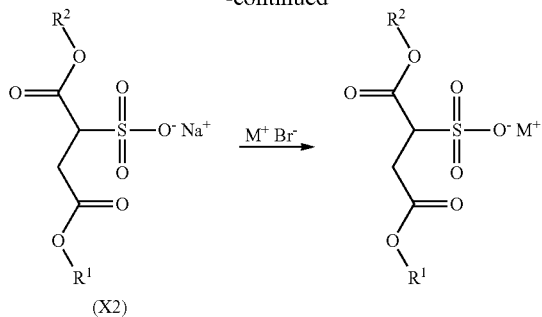

(X2)

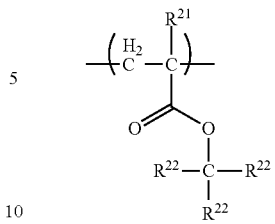

R, $R^1$, $R^2$, and $M^+$ in the above reaction formulas are the same as defined for R, $R^1$, $R^2$, and $M^+$ in the general formulas (0) and (1). The description given above in connection with R, $R^1$, $R^2$, and $M^+$ in the general formulas (0) and (1) may be applied to R, $R^1$, $R^2$, and $M^+$ in the above reaction formulas.

The radiation-sensitive composition according to one embodiment of the invention may include only one type of the acid generator (A), or may include two or more types of the acid generator (A).

The acid generator (A) is normally used in the radiation-sensitive composition according to one embodiment of the invention in an amount of 0.1 to 50 parts by mass, preferably 1 to 40 parts by mass, and more preferably 5 to 30 parts by mass, based on 100 parts by mass of a resin (B) and an acid-labile dissolution inhibitor compound (described below) in total. If the amount of the acid generator (A) is less than 0.1 parts by mass, the intended effects of the embodiment of the invention may not be sufficiently achieved. If the amount of the acid generator (A) exceeds 50 parts by mass, the transparency to radiation, the pattern shape, the heat resistance, and the like may deteriorate.

[1-2] Resin (B)

The radiation-sensitive composition according to one embodiment of the invention may further include a resin.

The resin (hereinafter may be referred to as "resin (B)") includes a repeating unit that includes an acid-labile group. The resin (B) is insoluble or scarcely soluble in an alkali, but becomes readily soluble in an alkali due to an acid. The expression "insoluble or scarcely soluble in an alkali" means that a film (thickness: 100 nm) formed only of the resin (B) has a thickness equal to or more than 50% of the initial thickness when developed under alkaline development conditions employed when forming a resist pattern using a resist film formed of a radiation-sensitive composition that includes the resin (B).

When the radiation-sensitive composition according to one embodiment of the invention includes the resin (B), the radiation-sensitive composition can produce a chemically-amplified positive-tone resist film that effectively responds to electron beams or extreme ultraviolet rays during a lithographic process, and can stably and accurately produce a fine pattern.

The acid-labile group included in the repeating unit included in the resin (B) dissociates due to an acid. The repeating unit is not particularly limited as long as the repeating unit has the above function, but is preferably at least one of a repeating unit shown by the following general formula (p-1) (hereinafter referred to as "repeating unit (p-1)") and a repeating unit shown by the following general formula (p-2) (hereinafter referred to as "repeating unit (p-2)").

Excellent sensitivity can be achieved by utilizing at least one of the repeating unit (p-1) and the repeating unit repeating unit (p-2) as the repeating unit that includes the acid-labile group.

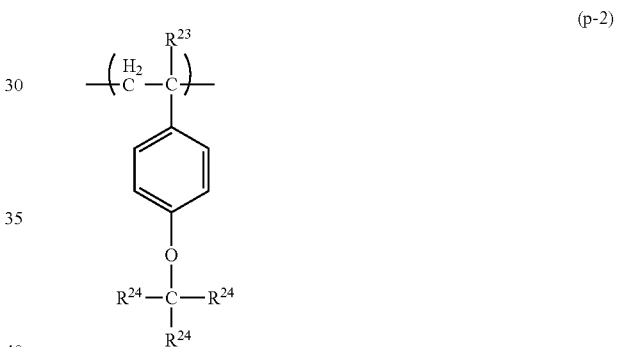

(p-1)

wherein $R^{21}$ represents a hydrogen atom, a methyl group, a trifluoromethyl group, or a hydroxymethyl group, and $R^{22}$ individually represent a linear or branched alkyl group having 1 to 4 carbon atoms, an aryl group having 6 to 22 carbon atoms, a monovalent alicyclic hydrocarbon group having 4 to 20 carbon atoms, or a group derived therefrom, or two of $R^{22}$ bond to each other to form a divalent alicyclic hydrocarbon group or a group derived therefrom together with the carbon atom that is bonded to the two $R^{22}$, and the remainder of $R^{22}$ represents a linear or branched alkyl group having 1 to 4 carbon atoms, an aryl group having 6 to 22 carbon atoms, a monovalent alicyclic hydrocarbon group having 4 to 20 carbon atoms, or a group derived therefrom.

(p-2)

wherein $R^{23}$ represents a hydrogen atom, a methyl group, a trifluoromethyl group, or a hydroxymethyl group, and $R^{24}$ individually represent a linear or branched alkyl group having 1 to 4 carbon atoms, a monovalent alicyclic hydrocarbon group having 4 to 20 carbon atoms, or a group derived therefrom, or two of $R^{24}$ bond to each other to form a divalent alicyclic hydrocarbon group or a group derived therefrom together with the carbon atom that is bonded to the two $R^{24}$, and the remainder of $R^{24}$ represents a linear or branched alkyl group having 1 to 4 carbon atoms, a monovalent alicyclic hydrocarbon group having 4 to 20 carbon atoms, or a group derived therefrom.

Examples of the linear or branched alkyl group having 1 to 4 carbon atoms represented by $R^{22}$ in the formula (p-1) include a methyl group, an ethyl group, an n-propyl group, an i-propyl group, an n-butyl group, a 2-methylpropyl group, a 1-methylpropyl group, a t-butyl group, and the like.

Examples of the monovalent alicyclic hydrocarbon group having 4 to 20 carbon atoms represented by $R^{22}$ in the general formula (p-1) include a group that includes an alicyclic ring derived from a cycloalkane such as norbornane, tricyclodecane, tetracyclododecane, adamantane, cyclobutane, cyclopentane, cyclohexane, cycloheptane, or cyclooctane, and the like. Examples of a group derived from the alicyclic hydrocarbon group include a group obtained by substituting the monovalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

Examples of the aryl group having 6 to 22 carbon atoms represented by $R^{22}$ in the general formula (p-1) include a group derived from any of the structures shown by the following formulas (x-1) to (x-3). When $R^{22}$ represents a group (i.e., naphthyl group) derived from the structure shown by the formula (x-2), $R^{22}$ may be bonded to the carbon atom included in —O—C($R^{22}$)$_3$ in the general formula (p-1) (i.e., the carbon atom that is bonded to the oxygen atom) at the 1-position or the 2-position. When $R^{22}$ represents a group (i.e., anthryl group) derived from the structure shown by the formula (x-3), $R^{22}$ may be bonded to the carbon atom included in —O—C($R^{22}$)$_3$ in the general formula (p-1) at the 1-position, the 2-position, or the 9-position. The aryl group may be substituted with a substituent. Specific examples of the substituent include a methyl group, an ethyl group, a hydroxyl group, a carboxyl group, a halogen atom (e.g., fluorine atom, chlorine atom, and bromine atom), an alkoxy group (e.g., methoxy group, ethoxy group, propoxy group, and butoxy group), an alkyloxycarbonyl group, and the like.

(x-1)

(x-2)

(x-3)

Examples of the divalent alicyclic hydrocarbon group that is formed by two of $R^{22}$ together with the carbon atom that is bonded to the two $R^{22}$ (i.e., the carbon atom bonded to the oxygen atom) include a divalent alicyclic hydrocarbon group having 4 to 20 carbon atoms, and the like. Specific examples of the divalent alicyclic hydrocarbon group include a group that includes an alicyclic ring derived from norbornane, tricyclodecane, tetracyclododecane, adamantane, cyclopentane, or cyclohexane, and the like. Examples of a group derived from the divalent alicyclic hydrocarbon group formed by two of $R^{22}$ include a group obtained by substituting the divalent alicyclic hydrocarbon group with at least one linear, branched, or cyclic alkyl group having 1 to 4 carbon atoms, such as a methyl group, an ethyl group, an n-propyl group, an i-propyl group, an n-butyl group, a 2-methylpropyl group, a 1-methylpropyl group, or a t-butyl group, and the like.

The repeating unit shown by the general formula (p-1) is preferably any of repeating units shown by the following general formulas (p-1-1) to (p-1-7), and more preferably the repeating unit shown by the following general formula (p-1-2), (p-1-3), or (p-1-4). When the resin (B) includes any of these repeating units, the resulting resist pattern exhibits a small degree of nano edge roughness.

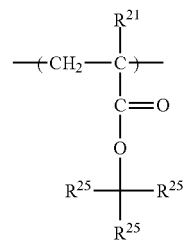
(p-1-1)

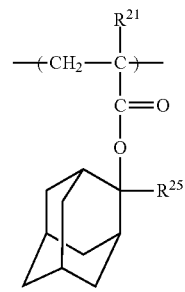
(p-1-2)

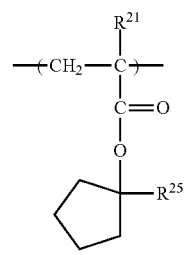
(p-1-3)

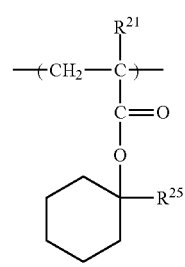
(p-1-4)

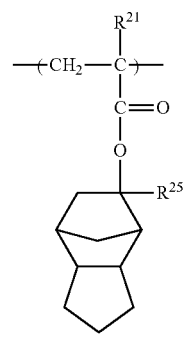
(p-1-5)

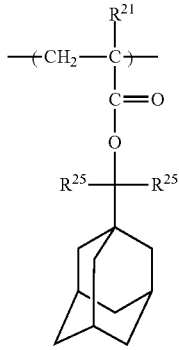

(p-1-6)

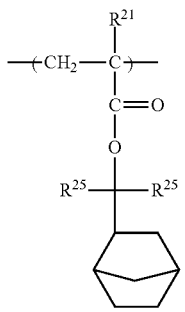

(p-1-7)

wherein $R^{21}$ represents a hydrogen atom, a methyl group, a trifluoromethyl group, or a hydroxymethyl group, and $R^{25}$ individually represent a linear or branched alkyl group having 1 to 4 carbon atoms or an aryl group having 6 to 22 carbon atoms.

The description given above in connection with the linear or branched alkyl group having 1 to 4 carbon atoms or the aryl group having 6 to 22 carbon atoms represented by $R^{22}$ in the general formula (p-1) may be applied to the linear or branched alkyl group having 1 to 4 carbon atoms or the aryl group having 6 to 22 carbon atoms represented by $R^{25}$ in the general formulas (p-1-1) to (p-1-7).

The resin (B) may include only one type of the repeating unit (p-1), or may include two or more types of the repeating unit (p-1).

The description given above in connection with the linear or branched alkyl group having 1 to 4 carbon atoms, the monovalent alicyclic hydrocarbon group having 4 to 20 carbon atoms, or a group derived therefrom represented by $R^{22}$ in the general formula (p-1), the divalent alicyclic hydrocarbon group formed by two of $R^{22}$ together with the carbon atom that is bonded to the two $R^{22}$, or a group derived therefrom may be applied to the linear or branched alkyl group having 1 to 4 carbon atoms, the monovalent alicyclic hydrocarbon group having 4 to 20 carbon atoms, or a group derived therefrom represented by $R^{24}$ in the general formula (p-2), the divalent alicyclic hydrocarbon group formed by two of $R^{24}$ together with the carbon atom that is bonded to the two $R^{24}$, or a group derived therefrom.

The repeating unit (p-2) is preferably a repeating unit shown by the following general formula (p-2-1). When the resin (B) includes the repeating unit shown by the general formula (p-2-1), the resulting resist pattern exhibits a small degree of nano edge roughness.

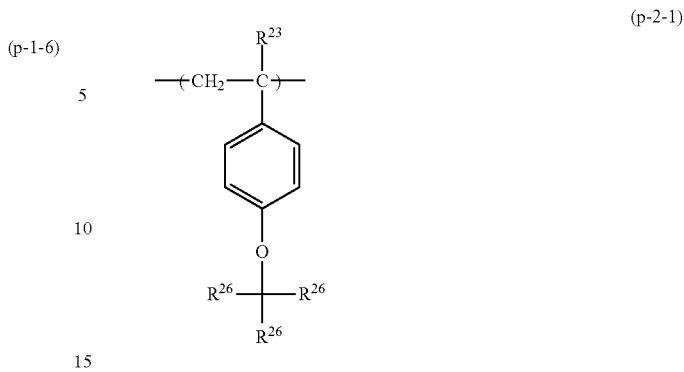

(p-2-1)

wherein $R^{23}$ represents a hydrogen atom, a methyl group, a trifluoromethyl group, or a hydroxymethyl group, and $R^{26}$ individually represent a linear or branched alkyl group having 1 to 4 carbon atoms.

The description given above in connection with the linear or branched alkyl group having 1 to 4 carbon atoms represented by $R^{22}$ in the general formula (p-1) may be applied to the linear or branched alkyl group having 1 to 4 carbon atoms represented by $R^{26}$ in the general formula (p-2-1).

The resin (B) may include only one type of the repeating unit (p-2), or may include two or more types of the repeating unit (p-2).

The resin (B) preferably includes at least one of repeating units shown by the following general formulas (b-1) to (b-5) in addition to the repeating units (p-1) and (p-2).

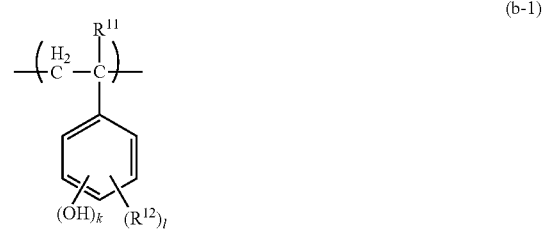

(b-1)

wherein $R^{11}$ represents a hydrogen atom or a methyl group, $R^{12}$ represents a linear or branched alkyl group having 1 to 12 carbon atoms or a linear or branched alkoxy group having 1 to 12 carbon atoms, k is an integer from 0 to 3, and l is an integer from 0 to 3, provided that $k+l \leq 5$ is satisfied,

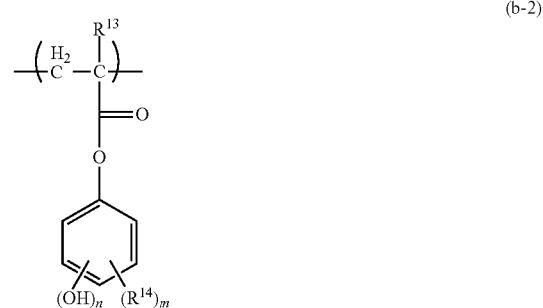

(b-2)

wherein $R^{13}$ represents a hydrogen atom or a methyl group, $R^{14}$ represents a linear or branched alkyl group having 1 to 12 carbon atoms or a linear or branched alkoxy group having 1 to 12 carbon atoms, m is an integer from 0 to 3, and n is an integer from 0 to 3, provided that m+n≤5 is satisfied,

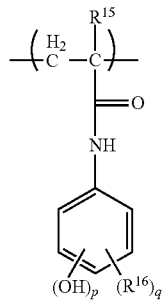
(b-3)

wherein $R^{15}$ represents a hydrogen atom or a methyl group, $R^{16}$ represents a linear or branched alkyl group having 1 to 12 carbon atoms or a linear or branched alkoxy group having 1 to 12 carbon atoms, p is an integer from 0 to 3, and q is an integer from 0 to 3, provided that p+q≤5 is satisfied,

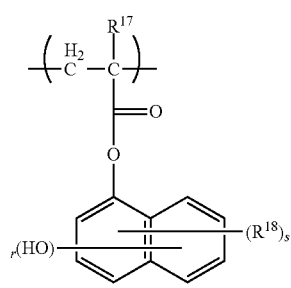
(b-4)

wherein $R^{17}$ represents a hydrogen atom or a methyl group, $R^{18}$ represents a linear or branched alkyl group having 1 to 12 carbon atoms or a linear or branched alkoxy group having 1 to 12 carbon atoms, r is an integer from 0 to 3, and s is an integer from 0 to 3,

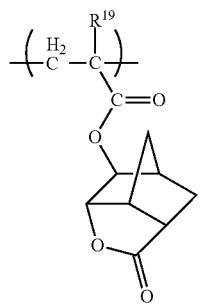
(b-5)

wherein $R^{19}$ represents a hydrogen atom or a methyl group.

When the resin (B) includes the repeating unit shown by the general formula (b-1) (hereinafter referred to as "repeating unit (b-1)"), the resulting resist pattern exhibits a small degree of nano edge roughness.

Examples of the linear or branched alkyl group having 1 to 12 carbon atoms represented by $R^{12}$ in the general formula (b-1) include a methyl group, an ethyl group, an n-propyl group, an i-propyl group, an n-butyl group, a 2-methylpropyl group, a 1-methylpropyl group, a t-butyl group, and the like. Among these, a methyl group, an ethyl group, an n-butyl group, and a t-butyl group are preferable since the nano edge roughness can be reduced.

Examples of the linear or branched alkoxy group having 1 to 12 carbon atoms represented by $R^{12}$ in the general formula (b-1) include a methoxy group, an ethoxy group, an n-propoxy group, an i-propoxy group, an n-butoxy group, a 2-methylpropoxy group, a 1-methylpropoxy group, a t-butoxy group, and the like. Among these, a methoxy group and an ethoxy group are preferable since the nano edge roughness can be reduced.

k in the general formula (b-1) is an integer from 0 to 3, and preferably 1 or 2. l is an integer from 0 to 3, and preferably an integer from 0 to 2.

Specific examples of the repeating unit (b-1) include the repeating units shown by the following formulas (b-1-1) to (b-1-4), and the like.

The resin (B) may include only one type of the repeating unit (b-1), or may include two or more types of the repeating unit (b-1).

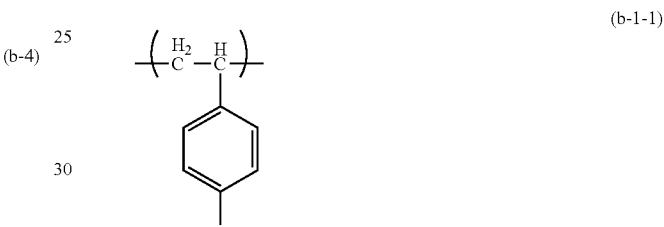
(b-1-1)

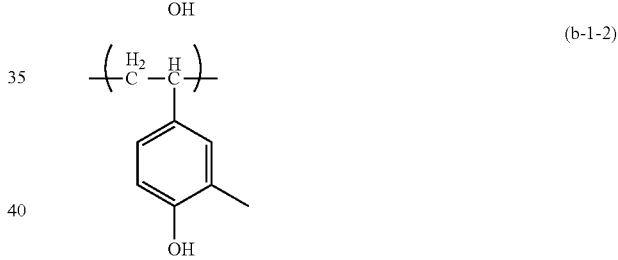
(b-1-2)

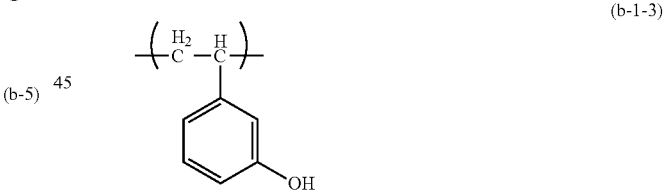
(b-1-3)

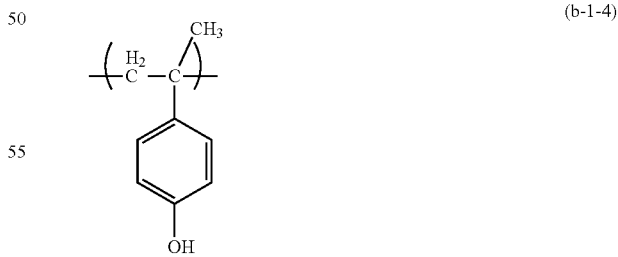
(b-1-4)

The repeating unit (b-1) may be obtained using the corresponding hydroxystyrene derivative as a monomer. The repeating unit (b-1) may also be obtained using a compound that produces the corresponding hydroxystyrene derivative via hydrolysis as a monomer.

Examples of the monomer used to produce the repeating unit (b-1) include p-acetoxystyrene, p-(1-ethoxy)styrene, p-isopropenylphenol, and the like. When using p-acetoxystyrene, the repeating unit (b-1) is produced by polymerizing p-acetoxystyrene, and hydrolyzing the side chain of the resulting polymer.

When the resin (B) includes the repeating unit shown by the general formula (b-2) (hereinafter referred to as "repeating unit (b-2)"), the resulting resist pattern exhibits a small degree of nano edge roughness.

Examples of the linear or branched alkyl group having 1 to 12 carbon atoms or the linear or branched alkoxy group having 1 to 12 carbon atoms represented by $R^{14}$ in the general formula (b-2) include those given above in connection with the linear or branched alkyl group having 1 to 12 carbon atoms or the linear or branched alkoxy group having 1 to 12 carbon atoms represented by $R^{12}$ in the general formula (b-1).

m in the general formula (b-2) is an integer from 0 to 3, and preferably 0 or 1. n is an integer from 0 to 3, and preferably 1 or 2.

Specific examples of the repeating unit (b-2) include the repeating units shown by the following formulas (b-2-1) and (b-2-2), and the like.

The resin (B) may include only one type of the repeating unit (b-2), or may include two or more types of the repeating unit (b-2).

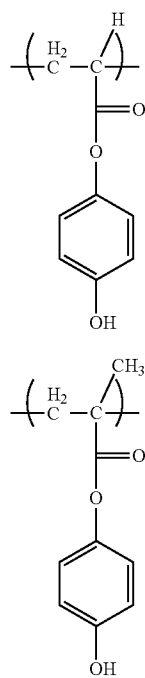

The repeating unit (b-2) may be obtained using the corresponding monomer.

Examples of the monomer used to produce the repeating unit (b-2) include 4-hydroxyphenyl acrylate, 4-hydroxyphenyl methacrylate, and the like.

When the resin (B) includes the repeating unit shown by the general formula (b-3) (hereinafter referred to as "repeating unit (b-3)"), the resulting resist pattern exhibits a small degree of nano edge roughness.

Examples of the linear or branched alkyl group having 1 to 12 carbon atoms or the linear or branched alkoxy group having 1 to 12 carbon atoms represented by $R^{16}$ in the general formula (b-3) include those given above in connection with the linear or branched alkyl group having 1 to 12 carbon atoms or the linear or branched alkoxy group having 1 to 12 carbon atoms represented by $R^{12}$ in the general formula (b-1).

p in the general formula (b-3) is an integer from 0 to 3, and preferably 1 or 2. q is an integer from 0 to 3, and preferably 0 or 1.

Specific examples of the repeating unit (b-3) include the repeating units shown by the following formulas (b-3-1) and (b-3-2), and the like.

The resin (B) may include only one type of the repeating unit (b-3), or may include two or more types of the repeating unit (b-3).

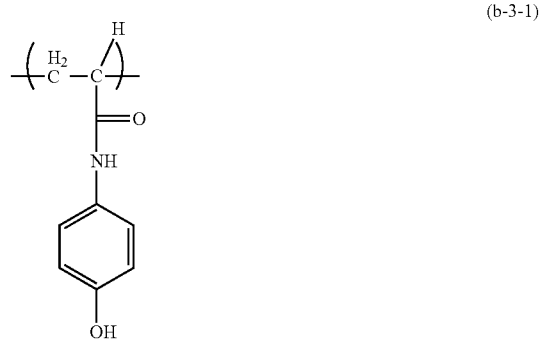

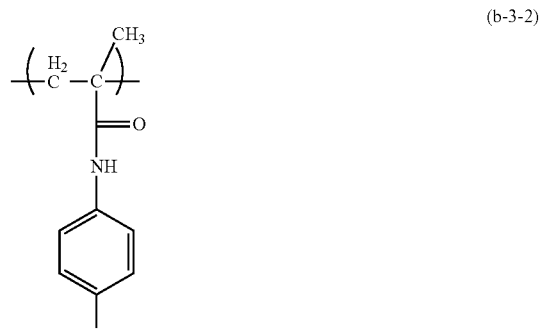

The repeating unit (b-3) may be obtained using the corresponding monomer.

Examples of the monomer used to produce the repeating unit (b-3) include N-(4-hydroxyphenyl)acrylamide, N-(4-hydroxyphenyl)methacrylamide, and the like.

When the resin (B) includes the repeating unit shown by the general formula (b-4) (hereinafter referred to as "repeating unit (b-4)"), the resulting resist pattern exhibits a small degree of nano edge roughness.

Examples of the linear or branched alkyl group having 1 to 12 carbon atoms or the linear or branched alkoxy group having 1 to 12 carbon atoms represented by $R^{18}$ in the general formula (b-4) include those given above in connection with the linear or branched alkyl group having 1 to 12 carbon atoms or the linear or branched alkoxy group having 1 to 12 carbon atoms represented by $R^{12}$ in the general formula (b-1).

r in the general formula (b-4) is an integer from 0 to 3, and preferably 1 or 2. s is an integer from 0 to 3, and preferably 0 or 1.

Specific examples of the repeating unit (b-4) include the repeating units shown by the following formulas (b-4-1) and (b-4-2), and the like.

The resin (B) may include only one type of the repeating unit (b-4), or may include two or more types of the repeating unit (b-4).

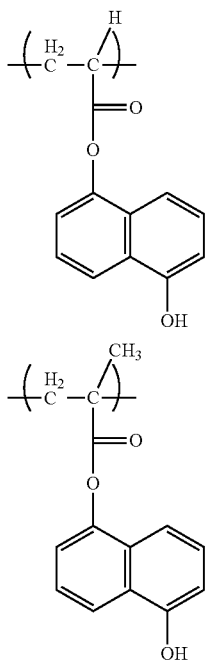

(b-4-1)

(b-4-2)

The repeating unit (b-3) may be obtained using the corresponding monomer.

Examples of the monomer used to produce the repeating unit (b-4) include 5-hydroxynaphthalen-1-yl methacrylate, 5-hydroxynaphthalen-1-yl acrylate, and the like.

When the resin (B) includes the repeating unit shown by the general formula (b-5) (hereinafter referred to as "repeating unit (b-5)"), the resulting resist pattern exhibits a small degree of nano edge roughness.

Specific examples of the repeating unit (b-5) include the repeating units shown by the following formulas (b-5-1) and (b-5-2), and the like.

The resin (B) may include only one type of the repeating unit (b-5), or may include two or more types of the repeating unit (b-5).

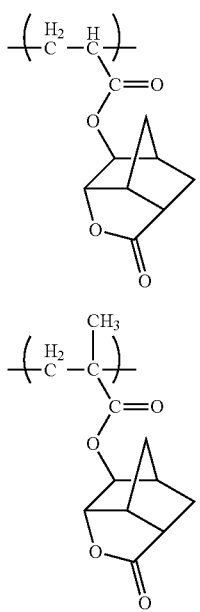

(b-5-1)

(b-5-2)

The repeating unit (b-5) may be obtained using the corresponding monomer.

Examples of the monomer used to produce the repeating unit (b-5) include compounds shown by the following general formulas (M-5-1) and (M-5-2), and the like.

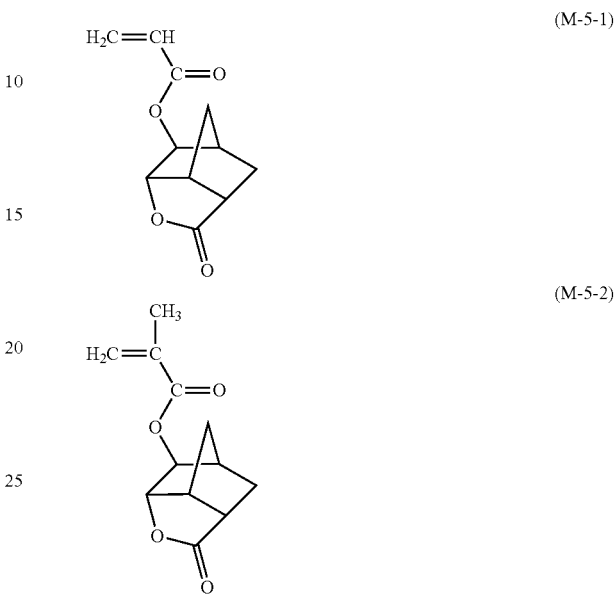

(M-5-1)

(M-5-2)

The resin (B) may further include a repeating unit derived from a non-acid-labile compound (i.e., a compound that does not include a group that dissociates due to an acid (acid-labile group)) (hereinafter referred to as "repeating unit (b-6)") in addition to the repeating units (p-1), (p-2), and (b-1) to (b-5).

When the resin (B) includes the repeating unit (b-6), the resulting resist pattern exhibits a small degree of nano edge roughness.

Examples of the non-acid-labile compound that produces the repeating unit (b-6) include styrene, α-methylstyrene, 4-methylstyrene, 2-methylstyrene, 3-methylstyrene, isobornyl acrylate, tricyclodecanyl(meth)acrylate, tetracyclododecenyl(meth)acrylate, and the like. Among these, styrene, α-methylstyrene, 4-methylstyrene, 2-methylstyrene, 3-methylstyrene, and tricyclodecanyl acrylate are preferable.

The resin (B) may include only one type of the repeating unit (b-6), or may include two or more types of the repeating unit (b-6).

The content of the repeating unit that includes the acid-labile group (particularly the total content of the repeating units (p-1) and (p-2)) in the resin (B) is preferably 1 mol % or more, more preferably 10 to 70 mol %, and still more preferably 20 to 60 mol %, based on the total amount (=100 mol %) of the repeating units included in the resin (B). If the content of the repeating unit that includes the acid-labile group is less than 1 mol %, nano edge roughness may occur to a large extent. If the content of the repeating unit that includes the acid-labile group is 1 mol % or more (particularly 10 to 70 mol %), a resist film that exhibits a small degree of nano edge roughness can be formed.

The total content of the repeating units (b-1) to (b-5) in the resin (B) is preferably 95 mol % or less, more preferably 1 to 95 mol %, still more preferably 10 to 95 mol %, and particularly preferably 40 to 80 mol %, based on the total amount (=100 mol %) of the repeating units included in the resin (B). If the total content of the repeating units (b-1) to (b-5) exceeds 95 mol %, nano edge roughness may occur to a large extent. If the total content of the repeating units (b-1) to (b-5) is 1 to 95 mol %, a resist film that exhibits a small degree of nano edge roughness can be formed.

The total content of the repeating units (p-1), (p-2), and (b-1) to (b-5) in the resin (B) is preferably 10 mol % or more, more preferably 40 to 100 mol %, and still more preferably 50 to 100 mol %, based on the total amount (=100 mol %) of the repeating units included in the resin (B). If the total content of the repeating units (p-1), (p-2), and (b-1) to (b-5) is less than 10 mol %, nano edge roughness may occur to a large extent. If the total content of the repeating units (p-1), (p-2), and (b-1) to (b-5) is 10 mol % or more, a resist film that exhibits a small degree of nano edge roughness can be formed.

The content of the repeating unit (b-6) in the resin (B) is preferably 60 mol % or less, and more preferably 0 to 50 mol %, based on the total amount (=100 mol %) of the repeating units included in the resin (B). If the content of the repeating unit (b-6) exceeds 60 mol %, nano edge roughness may occur to a large extent. If the content of the repeating unit (b-6) is 60 mol % or less, a resist film that exhibits high resolution and a small degree of nano edge roughness in a well-balanced manner can be formed.

The resin (B) may be produced (synthesized) by an arbitrary method. For example, the resin (B) may be produced by radical polymerization or anionic polymerization. The side-chain phenol moiety or naphthol moiety of the repeating units (b-1) to (b-4) may be obtained by hydrolyzing the resulting resin (B) (e.g., acetoxy group) in an organic solvent in the presence of a base or an acid.

For example, radical polymerization may be implemented by stirring and heating at least one of the monomer that produces the repeating unit (p-1) and the monomer that produces the repeating unit (p-2) optionally together with the monomers that respectively produce the repeating units (b-1) to (b-6) in an appropriate organic solvent under a nitrogen atmosphere in the presence of a radical initiator.

Examples of the radical initiator include azo compounds such as 2,2'-azobisisobutylonitrile, 2,2'-azobis(2,4-dimethylvaleronitrile), 2,2'-azobis(4-methoxy-2,4-dimethylvaleronitrile), 2,2'-azobismethylbutyronitrile, 2,2'-azobiscyclohexanecarbonitrile, cyanomethylethylazoformamide, 2,2'-azobis(methyl 2,4-dimethylpropanate), and 2,2'-azobiscyanovaleric acid; organic peroxides such as benzoyl peroxide, lauroyl peroxide, 1,1'-bis(t-butylperoxy)cyclohexane, 3,5,5-trimethylhexanoyl peroxide, and t-butyl peroxy-2-ethylhexanoate; hydrogen peroxide; and the like.

A polymerization promoter such as 2,2,6,6-tetramethyl-1-piperidinyloxy, iodine, a mercaptan, or a styrene dimer may optionally be used for radical polymerization.

The radical polymerization temperature is appropriately selected depending on the type of initiator and the like. For example, the radical polymerization temperature may be set to 50 to 200° C. When using an azo initiator or a peroxide initiator, the radical polymerization temperature is preferably determined so that the half-life of the initiator is about 10 minutes to about 30 hours, and more preferably about 30 minutes to about 10 hours.

The reaction time is determined depending on the type of initiator and the reaction temperature, but is preferably determined so that 50% or more of the initiator is consumed (generally about 0.5 to about 24 hours).

Anionic polymerization may be implemented by stirring at least one of the monomer that produces the repeating unit (p-1) and the monomer that produces the repeating unit (p-2) optionally together with the monomers that respectively produce the repeating units (b-1) to (b-6) in an appropriate organic solvent under a nitrogen atmosphere in the presence of an anionic initiator, and maintaining the mixture at a given temperature, for example.

Examples of the anionic initiator include organic alkali metals such as n-butyllithium, s-butyllithium, t-butyllithium, ethyllithium, ethylsodium, 1,1-diphenylhexyllithium, 1,1-diphenyl-3-methylpentyllithium, and the like.

The anionic polymerization temperature may be appropriately selected depending on the type of initiator and the like. When using an alkyllithium as the initiator, the anionic polymerization temperature is preferably −100 to 50° C., and more preferably −78 to 30° C.

The reaction time is determined depending on the type of initiator and the reaction temperature, but is preferably determined so that 50% or more of the initiator is consumed (generally about 0.5 to about 24 hours).

Note that the resin (B) may be produced by heating the monomers without using an initiator, or may be produced by cationic polymerization.

Examples of an acid used when introducing the side-chain phenol moiety or naphthol moiety of the repeating units (b-1) to (b-4) by hydrolyzing the side chain of the resin (B) include organic acids such as p-toluenesulfonic acid, a hydrate thereof, methanesulfonic acid, trifluoromethanesulfonic acid, malonic acid, oxalic acid, and 1,1,1-fluoroacetic acid; inorganic acids such as sulfuric acid, hydrochloric acid, phosphoric acid, and hydrobromic acid, pyridinium p-toluenesulfonate, ammonium p-toluenesulfonate, 4-methylpyridinium p-toluenesulfonate; and the like.

Examples of a base used for hydrolysis include inorganic bases such as potassium hydroxide, sodium hydroxide, sodium carbonate, and potassium carbonate, organic bases such as triethylamine, N-methyl-2-pyrrolidone, piperidine, and tetramethylammonium hydroxide, and the like.

Examples of the organic solvent used for polymerization and hydrolysis include ketones such as acetone, methyl ethyl ketone, and methyl amyl ketone; ethers such as diethyl ether and tetrahydrofuran (THF); alcohols such as methanol, ethanol, and propanol; aliphatic hydrocarbons such as hexane, heptane, and octane; aromatic hydrocarbons such as benzene, toluene, and xylene; alkyl halides such as chloroform, bromoform, methylene chloride, methylene bromide, and carbon tetrachloride; esters such as ethyl acetate, butyl acetate, ethyl lactate, propylene glycol monomethyl ether, propylene glycol monomethyl ether acetate, and cellosolve; aprotic polar solvents such as dimethylformamide, dimethyl sulfoxide, and hexamethylphosphoroamide; and the like.

Among these, acetone, methyl amyl ketone, methyl ethyl ketone, tetrahydrofuran, methanol, ethanol, propanol, ethyl acetate, butyl acetate, ethyl lactate, propylene glycol monomethyl ether, and propylene glycol monomethyl ether acetate are preferable.

The polystyrene-reduced weight average molecular weight (hereinafter may be referred to as "Mw") of the resin (B) determined by gel permeation chromatography (GPC) is preferably 3000 to 100,000, more preferably 3000 to 40,000, and still more preferably 3000 to 25,000.

The ratio (Mw/Mn) of the Mw to the polystyrene-reduced number average molecular weight (hereinafter may be referred to as "Mn") of the resin (B) determined by GPC is preferably 1 to 5, more preferably 1 to 3, and still more preferably 1 to 2.5.

The radiation-sensitive composition according to one embodiment of the invention may include only one type of the resin (B), or may include two or more types of the resin (B).

[1-3] Acid-Labile Dissolution Inhibitor Compound

The radiation-sensitive composition according to one embodiment of the invention may further include an acid-labile dissolution inhibitor compound.

The term "acid-labile dissolution inhibitor compound" used herein refers to a compound that includes at least two acid-labile groups in its structure, and includes at least eight atoms other than the acid-labile group that are bonded between acid-labile groups among the at least two acid-labile groups that are positioned at the longest distance.

Examples of a preferable acid-labile dissolution inhibitor compound include (a) a compound that includes at least two acid-labile groups in its structure, and includes at least ten (more preferably 11 or more, and still more preferably 12 or more) atoms other than the acid-labile group that are bonded between acid-labile groups among the at least two acid-labile groups that are positioned at the longest distance, and (b) a compound that includes at least three acid-labile groups in its structure, and includes at least nine (more preferably 10 or more, and still more preferably 11 or more) atoms other than the acid-labile group that are bonded between acid-labile groups among the at least three acid-labile groups that are positioned at the longest distance. The upper limit of the number of atoms other than an acid-labile group that are bonded between the acid-labile groups positioned at the longest distance is preferably 50, and more preferably 30.

If the acid-labile dissolution inhibitor compound includes three or more (preferably four or more (or two)) acid-labile groups, the dissolution inhibition capability is significantly improved when the acid-labile groups are positioned at a distance equal to or longer than a given distance.

Note that the distance between the acid-labile groups of the acid-labile dissolution inhibitor compound is indicated by the number of atoms other than the acid-labile group that are bonded to each other. For example, the distance between the acid-labile groups of the following compounds (1) and (2) corresponds to four atoms, and the distance between the acid-labile groups of the following compound (3) corresponds to twelve atoms.

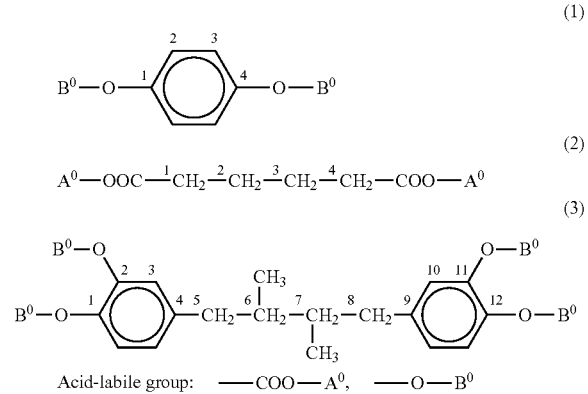

The acid-labile dissolution inhibitor compound may include a plurality of acid-labile groups that are bonded to one benzene ring. The acid-labile dissolution inhibitor compound preferably includes a skeleton in which one or two acid-labile groups are bonded to one benzene ring.

The molecular weight of the acid-labile dissolution inhibitor compound is 5000 or less, preferably 500 to 4000, and more preferably 1000 to 2500.

Examples of the acid-labile group include a group shown by —$R^0$—COO-$A^0$ or —Ar—O—$B^0$.

Note that $A^0$ represents —C($R^{01}$)($R^{02}$)($R^{03}$), —Si($R^{01}$)($R^{02}$)($R^{03}$), or —C($R^{04}$)($R^{05}$)—O—$R^{06}$. $B^0$ represents $A^0$ or —CO—O-$A^0$.

$R^{01}$, $R^{02}$, $R^{03}$, $R^{04}$, and $R^{05}$ individually represent a hydrogen atom, an alkyl group, a cycloalkyl group, an alkenyl group, or an aryl group, and $R^{06}$ represents an alkyl group or an aryl group. Note that at least two of $R^{01}$ to $R^{03}$ represent a group other than a hydrogen atom, and two of $R^{01}$ to $R^{03}$ or two of $R^{04}$ to $R^{06}$ may bond to form a ring. $R^0$ represents a divalent or higher valent aliphatic or aromatic hydrocarbon group that may be substituted with a substituent, and —Ar— represents a divalent or higher valent monocyclic or polycyclic aromatic group that may be substituted with a substituent.

Examples of a preferable alkyl group include alkyl groups having 1 to 4 carbon atoms, such as a methyl group, an ethyl group, a propyl group, an n-butyl group, an s-butyl group, and a t-butyl group. Examples of a preferable cycloalkyl group include cycloalkyl groups having 3 to 10 carbon atoms, such as a cyclopropyl group, a cyclobutyl group, a cyclohexyl group, and an adamantyl group. Examples of a preferable alkenyl group include alkenyl groups having 2 to 4 carbon atoms, such as a vinyl group, a propenyl group, an allyl group, and a butenyl group. Examples of a preferable aryl group include aryl groups having 6 to 14 carbon atoms, such as a phenyl group, a xylyl group, a tolyl group, a cumenyl group, a naphthyl group, and an anthracenyl group.

Examples of the substituent include a hydroxyl group, halogen atoms (fluorine atom, chlorine atom, bromine atom, and iodine atom), a nitro group, a cyano group, the above alkyl groups, alkoxy groups (e.g., methoxy group, ethoxy group, hydroxyethoxy group, propoxy group, hydroxypropoxy group, n-butoxy group, isobutoxy group, s-butoxy group, and t-butoxy group), alkoxycarbonyl groups (e.g., methoxycarbonyl group and ethoxycarbonyl group), aralkyl groups (e.g., benzyl group, phenethyl group, and cumyl group), aralkyloxy groups, acyl groups (e.g., formyl group, acetyl group, butyryl group, benzoyl group, cinnamyl group, and valeryl group), acyloxy groups (e.g., butyryloxy group), the above alkenyl groups, alkenyloxy groups (e.g., vinyloxy group, propenyloxy group, allyloxy group, and butenyloxy group), the above aryl groups, aryloxy groups (e.g., phenoxy group), and aryloxycarbonyl groups (e.g., benzoyloxy group).

Specific examples of a preferable acid-labile group include a silyl ether group, a cumyl ester group, an acetal group, a tetrahydropyranyl ether group, an enol ether group, an enol ester group, a tertiary alkyl ether group, a tertiary alkyl ester group, a tertiary alkyl carbonate group, and the like. Among these, a tertiary alkyl ester group, a tertiary alkyl carbonate group, a cumyl ester group, and a tetrahydropyranyl ether group are more preferable.

Examples of a preferable acid-labile dissolution inhibitor compound include compounds obtained by protecting some or all of the phenolic OH groups of the polyhydroxy compounds disclosed in Japanese Patent Application Publication (KOKAI) No. 1-289946, Japanese Patent Application Publication (KOKAI) No. 1-289947, Japanese Patent Application Publication (KOKAI) No. 2-2560, Japanese Patent Application Publication (KOKAI) No. 3-128959, Japanese Patent Application Publication (KOKAI) No. 3-158855, Japanese Patent Application Publication (KOKAI) No. 3-179353, Japanese Patent Application Publication (KOKAI) No. 3-191351, Japanese Patent Application Publication (KOKAI) No. 3-200251, Japanese Patent Application Publication (KOKAI) No. 3-200252, Japanese Patent Application Publication (KOKAI) No. 3-200253, Japanese Patent Application Publication (KOKAI) No. 3-200254, Japanese Patent Application Publication (KOKAI) No. 3-200255, Japanese Patent Application Publication (KOKAI) No. 3-259149, Japanese Patent Application Publication (KOKAI) No. 3-279958, Japanese Patent Application Publication (KOKAI) No. 3-279959, Japanese Patent Application Publication (KOKAI) No. 4-1650, Japanese Patent Application Publication (KOKAI) No. 4-1651, Japanese Patent Application Publication (KOKAI) No. 4-11260, Japanese Patent Application Publication (KOKAI) No. 4-12356, Japanese Patent Application Publication (KOKAI) No. 4-12357, Japanese Patent Application Publication (KOKAI) No. 4-271349, Japanese Patent Application Publication (KOKAI) No. 5-045869, Japanese Patent Application Publication (KOKAI) No. 5-158233, Japanese Patent Application Publication (KOKAI) No. 5-224409, Japanese Patent Application Publication (KOKAI) No. 5-257275, Japanese Patent Application Publication (KOKAI) No. 5-297581, Japanese Patent Application Publication (KOKAI) No. 5-297583, Japanese Patent Application Publication (KOKAI) No. 5-303197, Japanese Patent Application Publication (KOKAI) No. 05-303200, Japanese Patent Application Publication (KOKAI) No. 5-341510, and the like with —R$^O$—COO-A$^O$ or B$^O$.

Further examples of the acid-labile dissolution inhibitor compound include a compound shown by the following general formula (XX).

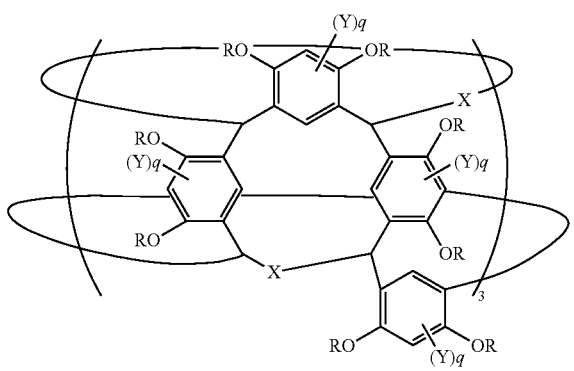

wherein R individually represent a hydrogen atom or a substituted or unsubstituted acid-labile group, X individually represent a substituted or unsubstituted alkylene group having 1 to 8 carbon atoms, Y individually represent a substituted or unsubstituted alkyl group having 1 to 10 carbon atoms, a substituted or unsubstituted alkenyl group having 2 to 10 carbon atoms, a substituted or unsubstituted alkynyl group having 2 to 10 carbon atoms, a substituted or unsubstituted aralkyl group having 7 to 10 carbon atoms, a substituted or unsubstituted alkoxy group having 1 to 10 carbon atoms, or a substituted or unsubstituted phenoxy group, and q are individually 0 or 1.

Examples of a preferable acid-labile dissolution inhibitor compound shown by the general formula (XX) include the compounds disclosed in Japanese Patent Application Publication (KOKAI) No. 2009-222920, and the like.

[1-4] Acid Diffusion Controller

The radiation-sensitive composition according to one embodiment of the invention preferably further includes an acid diffusion controller (hereinafter may be referred to as "acid diffusion controller (C)") in addition to the acid generator (A), the resin (B), and the acid-labile dissolution inhibitor compound.

The acid diffusion controller (C) controls a phenomenon in which an acid generated by the acid generator (A) upon exposure is diffused in the resist film, and suppresses undesired chemical reactions in the unexposed area.

The storage stability of the resulting radiation-sensitive composition is improved by adding the acid diffusion controller (C) to the radiation-sensitive composition. Moreover, the acid diffusion controller (C) further improves the resolution of the resulting resist, and suppresses a change in line width of the resist pattern due to a change in post-exposure delay (PED) from exposure to post-exposure bake, so that a radiation-sensitive composition that exhibits remarkably superior process stability can be obtained.

Examples of the acid diffusion controller (C) include nitrogen-containing organic compounds and photosensitive basic compounds.

Examples of the nitrogen-containing organic compounds include a compound shown by the following general formula (4) (hereinafter referred to as "nitrogen-containing compound (i)"), a compound that includes two nitrogen atoms in the molecule (hereinafter referred to as "nitrogen-containing compound (ii)"), a polyamino compound or a polymer that includes three or more nitrogen atoms (hereinafter collectively referred to as "nitrogen-containing compound (iii)"), an amide group-containing compound, a urea compound, a nitrogen-containing heterocyclic compound, and the like.

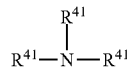

wherein R$^{41}$ individually represent a hydrogen atom, a substituted or unsubstituted linear, branched or cyclic alkyl group, a substituted or unsubstituted aryl group, or a substituted or unsubstituted aralkyl group.

Examples of the alkyl group represented by R$^{41}$ in the general formula (4) include a linear or branched alkyl group having 1 to 30 carbon atoms, a cyclic alkyl group having 3 to 30 carbon atoms, and the like. Specific examples of the alkyl group represented by R$^{41}$ in the general formula (4) include a methyl group, an ethyl group, an n-propyl group, an i-propyl group, an n-butyl group, a 2-methylpropyl group, a 1-methylpropyl group, a t-butyl group, a cyclopropyl group, a cyclopentyl group, a cyclohexyl group, an adamantyl group, a norbornyl group, and the like.

Examples of the aryl group represented by R$^{41}$ in the general formula (4) include an aryl group having 6 to 14 carbon atoms, and the like. Specific examples of the aryl group represented by R$^{41}$ in the general formula (4) include a phenyl group, a tolyl group, a naphthyl group, and the like.

Examples of the aralkyl group represented by R$^{41}$ in the general formula (4) include an aralkyl group having 6 to 12 carbon atoms, and the like. Specific examples of the aralkyl group represented by R$^{41}$ in the general formula (4) include a benzyl group, a phenethyl group, a naphthylmethyl group, a naphthylethyl group, and the like.

The alkyl group, the aryl group, and the aralkyl group may be substituted with a substituent. Specific examples of the substituent include a methyl group, an ethyl group, a propyl group, an n-butyl group, a t-butyl group, a hydroxyl group, a carboxyl group, a halogen atom (e.g., fluorine atom, chlorine atom, and bromine atom), an alkoxy group (e.g., methoxy group, ethoxy group, propoxy group, and butoxy group), and the like.

Examples of the nitrogen-containing compound (i) include mono(cyclo)alkylamines such as n-hexylamine, n-heptylamine, n-octylamine, n-nonylamine, n-decylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; tri(cyclo) alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, methyldicyclohexylamine, and tricyclohexylamine; and substituted alkylamines such as triethanolamine; aromatic amines such as aniline, N-methylaniline, N,N-dimethylaniline, 2-methylaniline, 3-methylaniline, 4-methylaniline, 4-nitroaniline, diphenylamine, triphenylamine, naphthylamine, 2,4,6-tri-tert-butyl-N-methylaniline, N-phenyldiethanolamine, 2,6-diisopropylaniline, 2-(4-aminophenyl)-2-(3-hydroxyphenyl)propane, 2-(4-aminophenyl)-2-(4-hydroxyphenyl)propane; and the like.

Examples of the nitrogen-containing compound (II) include ethylenediamine, N,N,N',N'-tetramethylethylenediamine, tetramethylenediamine, hexamethylenediamine, 4,4'-diaminodiphenylmethane, 4,4'-diamino diphenyl ether, 4,4'-diaminobenzophenone, 4,4'-diaminodiphenylamine, 2,2-bis (4-aminophenyl)propane, 2-(3-aminophenyl)-2-(4-aminophenyl)propane, 1,4-bis[1-(4-aminophenyl)-1-methylethyl]benzene, 1,3-bis[1-(4-aminophenyl)-1-methylethyl]benzene, bis(2-dimethylaminoethyl)ether, bis (2-diethylaminoethyl)ether, 1-(2-hydroxyethyl)-2-imidazolizinone, 2-quinoxalinol, N,N,N',N'-tetrakis(2-hydroxypropyl)ethylenediamine, and the like.

Examples of the nitrogen-containing compound (iii) include polyethyleneimine, polyallylamine, poly(2-dimethylaminoethylacrylamide), and the like.

Examples of the amide group-containing compound include N-t-butoxycarbonyl group-containing amino compounds such as N-t-butoxycarbonyl di-n-octylamine, N-t-butoxycarbonyl di-n-nonylamine, N-t-butoxycarbonyl di-n-decylamine, N-t-butoxycarbonyl dicyclohexylamine, N-t-butoxycarbonyl-1-adamantylamine, N-t-butoxycarbonyl-2-adamantylamine, N-t-butoxycarbonyl-N-methyl-1-adamantylamine, (S)-(−)-1-(t-butoxycarbonyl)-2-pyrrolidine methanol, (R)-(+)-1-(t-butoxycarbonyl)-2-pyrrolidine methanol, N-t-butoxycarbonyl-4-hydroxypiperidine, N-t-butoxycarbonylpyrrolidine, N-t-butoxycarbonylpiperazine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole, and N-t-butoxycarbonyl-2-phenylbenzimidazole, formamide, N-methylformamide, N,N-dimethylformamide, acetamide, N-methylacetamide, N,N-dimethylacetamide, propionamide, benzamide, pyrrolidone, N-methylpyrrolidone, N-acetyl-1-adamantylamine, tris(2-hydroxyethyl)isocyanuric acid, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include imidazoles such as imidazole, 4-methylimidazole, 4-methyl-2-phenylimidazole, benzimidazole, 2-phenylbenzimidazole, 1-benzyl-2-methylimidazole, and 1-benzyl-2-methyl-1H-imidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic acid amide, quinoline, 4-hydroxyquinoline, 8-oxyquinoline, acridine, and 2,2':6',2''-terpyridine; piperazines such as piperazine and 1-(2-hydroxyethyl)piperazine; and pyrazine, pyrazole, pyridazine, quinoxaline, purine, pyrrolidine, piperidine, piperidineethanol, 3-piperidino-1,2-propanediol, morpholine, 4-methylmorpholine, 1-(4-morpholinyl)ethanol, 4-acetylmorpholine, 3-(N-morpholino)-1,2-propanediol, 1,4-dimethylpiperazine, 1,4-diazabicyclo[2.2.2]octane, and the like.

The photosensitive basic compound is not particularly limited as long as the photosensitive basic compound has the above properties. Examples of the photosensitive basic compound include compounds shown by the following general formulas (5-1) and (5-2), and the like.

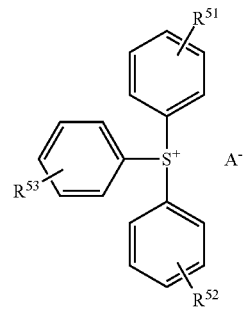

(5-1)

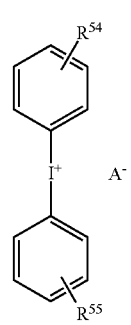

(5-2)

wherein $R^{51}$ to $R^{53}$ individually represent a hydrogen atom, a halogen atom, a substituted or unsubstituted alkyl group having 1 to 10 carbon atoms, a substituted or unsubstituted alicyclic hydrocarbon group, an —$OSO_2$—$R^{56}$ group, or an —$SO_2$—$R^{57}$ group, $R^{56}$ and $R^{57}$ represent a substituted or unsubstituted alkyl group having 1 to 10 carbon atoms, a substituted or unsubstituted alicyclic hydrocarbon group, or a substituted or unsubstituted aryl group, provided that two or more of $R^{51}$ to $R^{53}$ may bond to form a cyclic structure, $A^-$ in the general formula (5-1) represents $OH^-$, $R^{58}O^-$, or $R^{58}COO^-$, $R^{58}$ represents a monovalent organic group, $R^{54}$ and $R^{55}$ individually represent a hydrogen atom, a halogen atom, a substituted or unsubstituted alkyl group having 1 to 10 carbon atoms, or a substituted or unsubstituted alicyclic hydrocarbon group, A⁻ in the general formula (5-2) represents OH⁻, R⁵⁹O⁻, or R⁵⁹COO⁻, and R⁵⁹ represents a monovalent organic group.

Examples of the halogen atom represented by R⁵¹ to R⁵³ in the general formula (5-1) include a fluorine atom, a bromine atom, and the like. Examples of the unsubstituted alkyl group having 1 to 10 carbon atoms represented by R⁵¹ to R⁵⁷ in the general formulas (5-1) to (5-2) include a methyl group, an ethyl group, an n-propyl group, an i-propyl group, an n-butyl group, a 2-methylpropyl group, a 1-methylpropyl group, a t-butyl group, and the like. The alkyl group may be substituted with a hydroxyl group, a carboxyl group, a halogen atom (e.g., fluorine atom or bromine atom), an alkoxy group (e.g., methoxy group, ethoxy group, propoxy group, butoxy group, or t-butoxy group), an alkyloxycarbonyl group (e.g., t-butoxycarbonylmethyloxy group), or the like.

Examples of the unsubstituted alicyclic hydrocarbon group represented by R⁵¹ to R⁵⁷ include an alicyclic hydrocarbon group having 5 to 25 carbon atoms, and the like. Specific examples of the unsubstituted alicyclic hydrocarbon group represented by R⁵¹ to R⁵⁷ include a cyclopentyl group, a cyclohexyl group, and the like. The alicyclic hydrocarbon group may be substituted with a hydroxyl group, a carboxyl group, a halogen atom (e.g., fluorine atom or bromine atom), an alkoxy group (e.g., methoxy group, ethoxy group, propoxy group, butoxy group, or t-butoxy group), an alkyloxycarbonyl group (e.g., t-butoxycarbonylmethyloxy group), or the like.

Examples of the unsubstituted aryl group represented by R⁵⁶ and R⁵⁷ include an aryl group having 6 to 12 carbon atoms, and the like. Specific examples of the aryl group represented by R⁵⁶ and R⁵⁷ include a phenyl group, a naphthyl group, and the like. The aryl group may be substituted with a halogen atom (e.g., fluorine atom, chlorine atom, bromine atom, or iodine atom), a hydroxyl group, a thiol group, an alkyl group, an organic group that includes a heteroatom (e.g., halogen atom, oxygen atom, nitrogen atom, sulfur atom, phosphorus atom, or silicon atom), or the like.

R⁵¹ to R⁵⁵ in the general formulas (5-1) and (5-2) preferably represent a hydrogen atom, a methyl group, or a t-butyl group.

Examples of the monovalent organic group represented by R⁵⁸ and R⁵⁹ in A⁻ in the general formulas (5-1) to (5-2) include a substituted or unsubstituted alkyl group, a substituted or unsubstituted aryl group, and the like.

A⁻ preferably represents OH⁻, CH₃COO⁻, or any of the compounds shown by the following formulas (6-1) to (6-5).

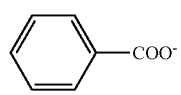

(6-1)

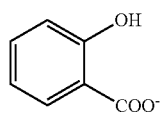

(6-2)

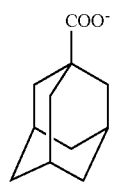

(6-3)

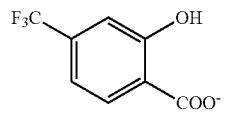

(6-4)

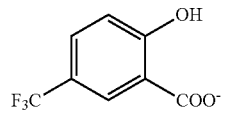

(6-5)

The photosensitive basic compound is preferably a triphenylsulfonium compound (i.e., the compound shown by the general formula (5-1)) wherein the anion moiety (A⁻) is OH⁻, CH₃COO⁻, or the compound shown by the formula (6-2), (6-3) or (6-4).

These acid diffusion controllers (C) may be used either individually or in combination.

The acid diffusion controller (C) is preferably used in an amount of 15 parts by mass or less, more preferably 0.001 to 10 parts by mass, and still more preferably 0.005 to 5 parts by mass, based on 100 parts by mass of the resin (B) and the acid-labile dissolution inhibitor compound in total. If the amount of the acid diffusion controller (C) exceeds 15 parts by mass, the sensitivity of the resulting resist film or the developability of the exposed area may deteriorate. If the amount of the acid diffusion controller (C) is less than 0.001 parts by mass, the pattern shape or the dimensional accuracy of the resulting resist film may deteriorate depending on the process conditions.

[1-5] Additional Photoacid Generator

The radiation-sensitive composition according to one embodiment of the invention may further include an additional photoacid generator other than the acid generator (A) (hereinafter may be referred to as "additional acid generator").

Examples of the additional acid generator include onium salt compounds, sulfonic acid compounds, and the like (excluding compounds that fall under the acid generator (A)).

Examples of the onium salt compounds include an iodonium salt, a sulfonium salt, a phosphonium salt, a diazonium salt, a pyridinium salt, and the like.

Specific examples of the onium salt compounds include diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl.2-oxocyclohexyl.methylsulfonium trifluoromethanesulfonate, dicyclohexyl.2-oxocyclohexylsulfonium trifluoromethanesulfonate, 2-oxocyclohexyldimethylsulfonium trifluoromethanesulfonate, bis(4-t-butylphenyl)iodonium nonafluorobutanesulfonate, bis(4-t-butylphenyl)iodonium trifluorobutanesulfonate, bis(4-t-butylphenyl)iodonium perfluorooctanesulfonate, bis(4-t-butylphenyl)iodonium p-toluenesulfonate, bis(4-t-butylphenyl)iodonium 10-camphorsulfonate, 4-trifluoromethylbenzenesulfonate, bis(4-t-butylphenyl)iodonium perfluorobenzenesulfonate, diphenyliodonium p-toluenesulfonate, diphenyliodonium benzenesulfonate, diphenyliodonium 10-camphorsulfonate, diphenyliodonium 4-trifluoromethylbenzenesulfonate, diphenyliodonium perfluorobenzenesulfonate, bis(p-fluorophenyl)iodonium trifluoromethanesulfonate, bis(p-fluorophenyl)iodonium nonafluoromethanesulfonate, bis(p-fluorophenyl)iodonium 10-camphorsulfonate, (p-fluorophenyl)(phenyl)iodonium trifluoromethanesulfonate, triphenylsulfonium nonafluorobutanesulfonate, triphenylsulfonium trifluoromethanesulfonate, triphenylsulfonium perfluorooctanesulfonate, triphenylsulfonium 2-bicyclo[2.2.1]hept-2-yl-1,1-difluoroethanesulfonate, triphenylsulfonium 2-bicyclo[2.2.1]hept-2-yl-1,1,2,2-tetrafluoroethanesulfonate, triphenylsulfonium p-toluenesulfonate, triphenylsulfonium benzenesulfonate, triphenylsulfonium 10-camphorsulfonate, triphenylsulfonium 4-trifluoromethylbenzenesulfonate, triphenylsulfonium perfluorobenzenesulfonate, 4-hydroxyphenyldiphenylsulfonium trifluoromethanesulfonate, tris(p-methoxyphenyl)sulfonium nonafluorobutanesulfonate, tris(p-methoxyphenyl)sulfonium trifluoromethanesulfonate, tris(p-methoxyphenyl)sulfonium perfluorooctanesulfonate, tris(p-methoxyphenyl)sulfonium p-toluenesulfonate, tris(p-methoxyphenyl)sulfonium benzenesulfonate, tris(p-methoxyphenyl)sulfonium 10-camphorsulfonate, tris(p-fluorophenyl)sulfonium trifluoromethanesulfonate, tris(p-fluorophenyl)sulfonium p-toluenesulfonate, (p-fluorophenyl)diphenylsulfonium trifluoromethanesulfonate, 4-butoxy-1-naphthyltetrahydrothiophenium nonafluorobutanesulfonate, 4-butoxy-1-naphthyltetrahydrothiophenium-2-bicyclo[2.2.1]hept-2-yl-1,1,2,2-tetrafluoroethanesulfonate, and the like.

Examples of the sulfonic acid compounds include alkyl sulfonates, alkylsulfonic acid imides, haloalkyl sulfonates, aryl sulfonates, imino sulfonates, and the like.

Specific examples of the sulfonic acid compounds include benzoin tosylate, tris(trifluoromethanesulfonate) of pyrogallol, nitrobenzyl-9,10-diethoxyanthracene-2-sulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimide trifluoromethanesulfonate, N-hydroxysuccinimide nonafluoro-n-butanesulfonate, N-hydroxysuccinimide perfluoro-n-octanesulfonate, 1,8-naphthalenedicarboxylic acid imide trifluoromethanesulfonate, 1,8-naphthalenedicarboxylic acid imide nonafluoro-n-butanesulfonate, 1,8-naphthalenedicarboxylic acid imide perfluoro-n-octanesulfonate, and the like.

Among these additional acid generators, diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl-2-oxocyclohexylmethylsulfonium trifluoromethanesulfonate, dicyclohexyl-2-oxocyclohexylsulfonium trifluoromethanesulfonate, 2-oxocyclohexyldimethylsulfonium trifluoromethanesulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimide trifluoromethanesulfonate, N-hydroxysuccinimide nonafluoro-n-butanesulfonate, N-hydroxysuccinimide perfluoro-n-octanesulfonate, 1,8-naphthalenedicarboxylic acid imide trifluoromethanesulfonate, triphenylsulfonium nonafluorobutanesulfonate, triphenylsulfonium trifluoromethanesulfonate, triphenylsulfonium 2-bicyclo[2.2.1]hept-2-yl-1,1-difluoroethanesulfonate, triphenylsulfonium 2-bicyclo[2.2.1]hept-2-yl-1,1,2,2-tetrafluoroethanesulfonate, 4-butoxy-1-naphthyltetrahydrothiophenium nonafluorobutanesulfonate, and 4-butoxy-1-naphthyltetrahydrothiophenium 2-bicyclo[2.2.1]hept-2-yl-1,1,2,2-tetrafluoroethanesulfonate are preferable.

These additional acid generators may be used either individually or in combination.

The additional acid generator is preferably used in an amount of 0 to 80 parts by mass, and more preferably 0 to 50 parts by mass, based on 100 parts by mass of the acid generator (A), in order to ensure that a resist film formed using the resulting radiation-sensitive composition exhibits excellent sensitivity and developability. If the amount of the additional acid generator exceeds 80 parts by mass, the resolution of the radiation-sensitive composition may deteriorate.

[1-6] Additional Component

The radiation-sensitive composition according to one embodiment of the invention may further include a solvent or an additive (e.g., surfactant, sensitizer, or aliphatic additive) in addition to the acid generator (A), the resin (B), the acid diffusion controller (C), and the additional acid generator.

Examples of the solvent include ethylene glycol monoalkyl ether acetates such as ethylene glycol monomethyl ether acetate, ethylene glycol monoethyl ether acetate, ethylene glycol mono-n-propyl ether acetate, and ethylene glycol mono-n-butyl ether acetate; propylene glycol monoalkyl ethers such as propylene glycol monomethyl ether, propylene glycol monoethyl ether, propylene glycol mono-n-propyl ether, and propylene glycol mono-n-butyl ether; propylene glycol dialkyl ethers such as propylene glycol dimethyl ether, propylene glycol diethyl ether, propylene glycol di-n-propyl ether, and propylene glycol di-n-butyl ether; propylene glycol monoalkyl ether acetates such as propylene glycol monomethyl ether acetate, propylene glycol monoethyl ether acetate, propylene glycol mono-n-propyl ether acetate, and propylene glycol mono-n-butyl ether acetate;

lactates such as methyl lactate, ethyl lactate, n-propyl lactate, and i-propyl lactate; formates such as n-amyl formate and i-amyl formate; acetates such as ethyl acetate, n-propyl acetate, i-propyl acetate, n-butyl acetate, i-butyl acetate, n-amyl acetate, i-amyl acetate, 3-methoxybutyl acetate, and 3-methyl-3-methoxybutyl acetate; propionates such as i-propyl propionate, n-butyl propionate, i-butyl propionate, and 3-methyl-3-methoxybutyl propionate; other esters such as ethyl hydroxyacetate, ethyl 2-hydroxy-2-methylpropionate, methyl 2-hydroxy-3-methylbutyrate, ethyl methoxyacetate, ethyl ethoxyacetate, methyl 3-methoxypropionate, ethyl 3-methoxypropionate, methyl 3-ethoxypropionate, ethyl 3-ethoxypropionate, 3-methyl-3-methoxybutyl butyrate, methyl acetoacetoate, ethyl acetoacetate, methyl pyruvate, and ethyl pyruvate; aromatic hydrocarbons such as toluene and xylene;

ketones such as methyl ethyl ketone, 2-pentanone, 2-hexanone, 2-heptanone, 3-heptanone, 4-heptanone, and cyclohexanone; amides such as N-methylformamide, N,N-dimethylformamide, N-methylacetamide, N,N-dimethylacetamide, and N-methylpyrrolidone; lactones such as γ-butyrolactone; and the like. These solvents may be used either individually or in combination.

It is preferable that the radiation-sensitive composition include at least one compound selected from ethylene glycol monoalkyl ether acetates and propylene glycol monoalkyl ether acetates as the solvent from the viewpoint of applicability.

The radiation-sensitive composition preferably includes at least one compound selected from ethylene glycol monoalkyl ether acetates and propylene glycol monoalkyl ether acetates in an amount of 70 to 100 parts by mass, and more preferably 70 to 80 parts by mass, based on 100 parts by mass of the solvent in total.

The solvent is preferably used so that the total solid content of the radiation-sensitive composition is 1 to 70 mass %, more preferably 1 to 15 mass %, and still more preferably 1 to 10 mass %. If the solvent is used so that the total solid content is within the above range, it is possible to prevent a situation in which the applicability of the radiation-sensitive composition is impaired due to an increase in viscosity. This makes it possible to form a resist film having a sufficient thickness.

The radiation-sensitive composition according to one embodiment of the invention may be prepared by homogeneously dissolving the acid generator (A) and the resin(B) in the solvent optionally together with the acid diffusion controller (C), the additional acid generator, and an additive (e.g., surfactant) so that the total solid content is within the above range. The radiation-sensitive composition thus prepared is preferably filtered through a filter having a pore size of about 0.2 μm, for example.

The surfactant improves the applicability, striation, developability, and the like of the radiation-sensitive composition.

Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate, and polyethylene glycol distearate; commercially available products such as KP341 (manufactured by Shin-Etsu Chemical Co., Ltd.), Polyflow No. 75, Polyflow No. 95 (manufactured by Kyoeisha Chemical Co., Ltd.), EFTOP EF301, EFTOP EF303, EFTOP EF352 (manufactured by JEMCO, Inc.), Megafac F171, Megafac F173 (manufactured by DIC Corporation), Fluorad FC430, Fluorad FC431 (manufactured by Sumitomo 3M Ltd.), Asahi Guard AG710, Surflon S-382, Surflon SC-101, Surflon SC-102, Surflon SC-103, Surflon SC-104, Surflon SC-105, Surflon SC-106 (manufactured by Asahi Glass Co., Ltd.), and the like. These surfactants may be used either individually or in combination.

The surfactant is preferably used in an amount of 2 parts by mass or less, and more preferably 0.001 to 2 parts by mass, based on 100 parts by mass of the resin (B) and the acid-labile dissolution inhibitor compound in total.

The sensitizer absorbs the energy of radiation, and transmits the energy to the acid generator (A), so that the amount of acid generated increases. Specifically, the sensitizer improves the apparent sensitivity of the radiation-sensitive composition.

Examples of the sensitizer include carbazoles, acetophenones, benzophenones, naphthalenes, phenols, biacetyl, eosine, rose bengal, pyrenes, anthracenes, phenothiazines, and the like. These sensitizers may be used either individually or in combination.

The sensitizer is preferably used in an amount of 20 parts by mass or less, and more preferably 0.1 to 20 parts by mass, based on 100 parts by mass of the resin (B) and the acid-labile dissolution inhibitor compound in total.

Examples of other additives include a dye or a pigment, and an adhesion improver. A dye or a pigment visualizes the latent image in the exposed area, and reduces the effects of halation during exposure. An adhesion improver improves the adhesion of the resist film to a substrate.

The alicyclic additive further improves the dry etching resistance, the pattern shape, adhesion to a substrate, and the like of the radiation-sensitive composition.

Examples of the alicyclic additive include adamantane derivatives such as 1-adamantanecarboxylic acid, 2-adamantanone, t-butyl-1-adamantanecarboxylate, t-butoxycarbonylmethyl 1-adamantanecarboxylate, α-butyrolactone 1-adamantanecarboxylate, di-t-butyl 1,3-adamantanedicarboxylate, t-butyl 1-adamantaneacetate, t-butoxycarbonylmethyl 1-adamantaneacetate, di-t-butyl 1,3-adamantanediacetate, and 2,5-dimethyl-2,5-di(adamantylcarbonyloxy)hexane; deoxycholates such as t-butyl deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, and mevalonolactone lithocholate; 3-(2-hydroxy-2,2-bis(trifluoromethyl)ethyl)tetracyclo[6.2.1.$1^{3,6}.0^{2.7}$]dodecane; and the like. These alicyclic additives may be used either individually or in combination.

The alicyclic additive is preferably used in an amount of 20 parts by mass or less, and more preferably 0.5 to 20 parts by mass, based on 100 parts by mass of the resin (B) and the acid-labile dissolution inhibitor compound in total. If the amount of the alicyclic additive exceeds 20 parts by mass, the heat resistance of the resulting resist film may deteriorate.

Examples of further additives include an alkali-soluble polymer, a low-molecular-weight alkali solubility controller that includes an acid-labile protecting group, a halation inhibitor, a preservative, an antifoaming agent, and the like.

[2] Resist Pattern-Forming Method

The radiation-sensitive composition according to one embodiment of the invention may be useful as a material for forming a chemically-amplified positive-tone resist film. For example, when forming a chemically-amplified positive-tone resist film using the radiation-sensitive composition that includes the resin (B), the acid-labile group included in the resin (B) dissociates due to an acid generated by the acid generator (A) upon exposure, so that the resin (B) becomes alkali-soluble. Specifically, an alkali-soluble area is formed in the resist film. The alkali-soluble area corresponds to the exposed area of the resist. The exposed area can be dissolved and removed using an alkaline developer. A positive-tone resist pattern having a desired shape can thus be obtained. The resist pattern-forming method is described in detail below.

When forming a resist pattern using the radiation-sensitive composition according to one embodiment of the invention, a resist film is formed using the radiation-sensitive composition.

The radiation-sensitive composition may be filtered through a filter having a pore size of about 0.2 μm after adjusting the total solid content, for example. The radiation-sensitive composition is applied to a substrate (e.g., silicon wafer or aluminum-coated wafer) using an appropriate application method (e.g., rotational coating, cast coating, or roll coating) to form a resist film. The resist film may optionally be pre-baked (PB) at about 70 to 160° C.

The resist film is then exposed to form a desired resist pattern. Examples of radiation that may be used for exposure include (extreme) deep ultraviolet rays such as KrF excimer laser light (wavelength: 248 nm), ArF excimer laser light (wavelength: 193 nm), EUV (extreme ultraviolet rays, wavelength: 13.5 nm), X-rays such as synchrotron radiation, charged particle rays such as electron beams, and the like. The exposure conditions (e.g., dose) may be appropriately determined depending on the composition of the radiation-sensitive composition, the type of additive, and the like. Note that liquid immersion lithography may also be used as the exposure process.

The resist film is preferably subjected to post-exposure bake (PEB) after exposure. PEB ensures smooth dissociation of the acid-labile group included in the resin (B). The PEB temperature may be appropriately selected depending on the components (composition) of the radiation-sensitive composition, but is preferably 30 to 200° C., and more preferably 50 to 170° C.

In order to maximize the potential of the radiation-sensitive composition, an organic or inorganic anti-reflective film may be formed on the substrate, as disclosed in Japanese Examined Patent Publication (KOKOKU) No. 6-12452 (Japanese Patent Application Publication (KOKAI) No. 59-93448), for example. A protective film may be formed on the resist film so that the resist film is not affected by basic impurities and the like contained in the environmental atmosphere, as disclosed in Japanese Patent Application Publication (KOKAI) No. 5-188598, for example. Note that these techniques may be used in combination.

The exposed resist film is developed to form a given resist pattern. A developer used for development is preferably an aqueous alkaline solution prepared by dissolving at least one alkaline compound (e.g., sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, or 1,5-diazabicyclo-[4.3.0]-5-nonene) in water.

The concentration of the alkaline aqueous solution is preferably 10 mass % or less. If the concentration of the alkaline aqueous solution exceeds 10 mass %, the unexposed area may be dissolved in the developer. The pH of the developer is preferably 8 to 14, and more preferably 9 to 14.

An organic solvent may be added to the alkaline aqueous solution (developer), for example. Examples of the organic solvent include ketones such as acetone, methyl ethyl ketone, methyl i-butyl ketone, cyclopentanone, cyclohexanone, 3-methylcyclopentanone, and 2,6-dimethylcyclohexanone; alcohols such as methanol, ethanol, n-propyl alcohol, i-propyl alcohol, n-butyl alcohol, t-butyl alcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonylacetone, dimethylformamide; and the like. These organic solvents may be used either individually or in combination.

The organic solvent is preferably used in an amount of 100 parts by volume or less based on 100 parts by volume of the alkaline aqueous solution. If the amount of the organic solvent exceeds 100 parts by volume, the exposed area may remain undeveloped due to a decrease in developability. An appropriate amount of a surfactant or the like may also be added to the alkaline aqueous solution (developer). After developing the resist film using the alkaline aqueous solution (developer), the resist film may be rinsed with water, and dried.

[3] Photoacid Generator

A photoacid generator according to one embodiment of the invention includes the partial structure shown by the general formula (0) (preferably the partial structure shown by the general formula (1)). The description given above in connection with the photoacid generator (A) included in the radiation-sensitive composition according to one embodiment of the invention may be applied to the photoacid generator according to one embodiment of the invention.

The photoacid generator according to one embodiment of the invention exhibits high solubility in a solvent, and may suitably be used as the photoacid generator (A) included in the radiation-sensitive composition according to one embodiment of the invention.

EXAMPLES

The embodiments of the invention are further described below by way of examples. Note that the invention is not limited to the following examples. In the examples, "parts" and "%" respectively refer to "parts by mass" and "mass %", unless otherwise specified. In the examples, electron beams (EB) were used to expose the resist film. Note that similar basic resist properties are obtained using short-wavelength radiation (e.g., EUV), and a correlation is observed between the basic resist properties obtained using electron beams (EB) and the basic resist properties obtained using short-wavelength radiation (e.g., EUV).

[1] Synthesis of Resin

Synthesis Example 1

Synthesis of Resin (B-1)

55 g of p-acetoxystyrene, 45 g of the compound shown by the following formula (M-1) (hereinafter may be referred to as "compound (M-1)"), 4 g of azobisisobutylonitrile, and 1 g of t-dodecylmercaptan were dissolved in 100 g of propylene glycol monomethyl ether. The compounds were polymerized at 70° C. for 16 hours in a nitrogen atmosphere. After completion of polymerization, the reaction solution was added dropwise to 1000 g of n-hexane to coagulate and purify the copolymer. After the addition of 150 g of propylene glycol monomethyl ether to the copolymer, 150 g of methanol, 34 g of triethylamine, and 6 g of water were added to the mixture. The mixture was hydrolyzed at the boiling point for 8 hours under reflux. After completion of the reaction, the solvent and triethylamine were evaporated under reduced pressure. After dissolving the resulting copolymer in 150 g of acetone, the solution was added dropwise to 2000 g of water to coagulate the copolymer. A white powder thus produced was filtered, and dried at 50° C. overnight under reduced pressure.

The resulting copolymer had an Mw of 10,000 and a dispersity (Mw/Mn) of 2.1. The molar ratio of repeating units derived from p-hydroxystyrene and repeating units derived from the compound (M-1) in the copolymer determined by $^{13}$C-NMR analysis was 65:35. This copolymer is hereinafter referred to as "resin (B-1)".

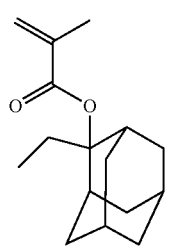

(M-1)

Synthesis Example 2

Synthesis of Resin (B-2)

5.5 g of p-acetoxystyrene, 4.5 g of the compound shown by the following formula (M-2) (hereinafter may be referred to as "compound (M-2)"), and 1.0 g of azobisisobutylonitrile were dissolved in 15 g of propylene glycol monomethyl ether. The compounds were polymerized at 70° C. for 16 hours in a nitrogen atmosphere. After completion of polymerization, the reaction solution was added dropwise to 500 g of n-hexane to coagulate and purify the copolymer. After the addition of 7.5 g of propylene glycol monomethyl ether to the copolymer, 15 g of methanol, 4.0 g of triethylamine, and 1.0 g of water were added to the mixture. The mixture was hydrolyzed at the boiling point for 8 hours under reflux. After completion of the reaction, the solvent and triethylamine were evaporated under reduced pressure. After dissolving the resulting copolymer in 10 g of acetone, the solution was added dropwise to 100 g of water to coagulate the copolymer. A white powder thus produced was filtered, and dried at 50° C. overnight under reduced pressure.

The resulting copolymer had an Mw of 4000 and a dispersity (Mw/Mn) of 2.4. The molar ratio of repeating units derived from p-acetoxystyrene and repeating units derived from the compound (M-2) in the copolymer determined by $^{13}$C-NMR analysis was 65:35. This copolymer is hereinafter referred to as "resin (B-2)".

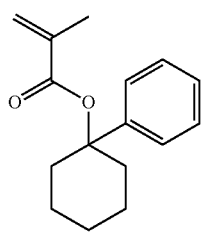

(M-2)

Synthesis Example 3

Synthesis of Resin (B-3)

53 g of p-acetoxystyrene, 47 g of the compound shown by the following formula (M-3) (hereinafter may be referred to as "compound (M-3)"), 4 g of azobisisobutylonitrile, and 0.2 g of t-dodecylmercaptan were dissolved in 200 g of propylene glycol monomethyl ether. The compounds were polymerized at 70° C. for 6 hours in a nitrogen atmosphere. After completion of polymerization, the reaction solution was added dropwise to 2000 g of n-hexane to coagulate and purify the copolymer. After the addition of 150 g of propylene glycol monomethyl ether to the copolymer, 150 g of methanol, 37 g of triethylamine, and 7 g of water were added to the mixture. The mixture was hydrolyzed at the boiling point for 8 hours under reflux. After completion of the reaction, the solvent and triethylamine were evaporated under reduced pressure. After dissolving the resulting copolymer in 150 g of acetone, the solution was added dropwise to 2000 g of water to coagulate the copolymer. A white powder thus produced was filtered, and dried at 50° C. overnight under reduced pressure.

The resulting copolymer had an Mw of 13,000 and a dispersity (Mw/Mn) of 2.4. The molar ratio of repeating units derived from p-acetoxystyrene and repeating units derived from the compound (M-3) in the copolymer determined by $^{13}$C-NMR analysis was 50:50. This copolymer is hereinafter referred to as "resin (B-3)".

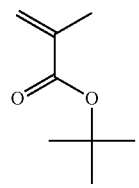

(M-3)

Synthesis Example 4

Synthesis of Resin (B-4)

57 g of the compound shown by the formula (M-4) (hereinafter may be referred to as "compound (M-4)"), 43 g of the compound shown by the following formula (M-5) (hereinafter may be referred to as "compound (M-5)"), and 4 g of azobisisobutylonitrile were dissolved in 300 g of methyl ethyl ketone. The compounds were polymerized at 78° C. for 6 hours in a nitrogen atmosphere. After completion of polymerization, the reaction solution was added dropwise to 2000 g of methanol to coagulate the copolymer. The copolymer (white powder) was washed twice with 300 g of methanol, filtered, and dried at 50° C. overnight under reduced pressure.

The resulting copolymer had an Mw of 8000 and a dispersity (Mw/Mn) of 2.5. The molar ratio of repeating units derived from the compound (M-4) and repeating units derived from the compound (M-5) in the copolymer determined by $^{13}$C-NMR analysis was 48:52. This copolymer is hereinafter referred to as "resin (B-4)".

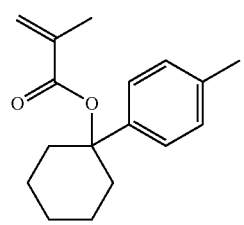

(M-4)

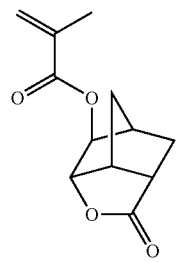

(M-5)

Synthesis Example 5

Synthesis of Resin (B-5)

55 g of the compound (M-5), 45 g of the compound shown by the following formula (M-6) (hereinafter may be referred to as "compound (M-6)"), and 3 g of azobisisobutylonitrile were dissolved in 300 g of methyl ethyl ketone. The compounds were polymerized at 78° C. for 6 hours in a nitrogen atmosphere. After completion of polymerization, the reaction solution was added dropwise to 2000 g of methanol to coagulate the copolymer. The copolymer (white powder) was washed twice with 300 g of methanol, filtered, and dried at 50° C. overnight under reduced pressure.

The resulting copolymer had an Mw of 7000 and a dispersity (Mw/Mn) of 2.1. The molar ratio of repeating units derived from the compound (M-5) and repeating units derived from the compound (M-6) in the copolymer determined by $^{13}$C-NMR analysis was 52:47. This copolymer is hereinafter referred to as "resin (B-5)".

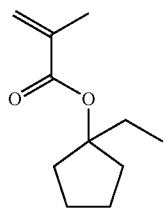

(M-6)

Note that the weight average molecular weight (Mw) and the number average molecular weight (Mn) were determined by gel permeation chromatography (GPC) using GPC columns manufactured by Tosoh Corporation (G2000HXL×2, G3000HXL×1, G4000HXL×1) (flow rate: 1.0 ml/min, eluant: tetrahydrofuran, column temperature: 40° C., standard: monodisperse polystyrene). The dispersity (Mw/Mn) was calculated from the measurement results.

The copolymer was subjected to $^{13}$C-NMR analysis using a mass spectrometer "JNM-EX270" (manufactured by JEOL Ltd.).

[2] Preparation of Radiation-Sensitive Composition

Example 1

100 parts of the resin (B-1) obtained in Synthesis Example 1, 27 parts of an acid generator (A-1), 2 parts of an acid diffusion controller (C-1), 1400 parts of a solvent (D-1), and 3300 parts of a solvent (D-2) were mixed (see Table 1). The mixture was filtered through a membrane filter (pore size: 200 nm) to obtain a composition solution (radiation-sensitive composition of Example 1).

Examples 2 to 12 and Comparative Examples 1 to 3

The resin (B), the acid generator (A), the acid diffusion controller (C), and the solvent (D) were mixed in the ratio shown in Table 1. The resulting mixture was filtered through a membrane filter (pore size: 200 nm) to obtain composition solutions (radiation-sensitive compositions) of Examples 2 to 12 and Comparative Examples 1 to 3.

TABLE 1

|  | Resin (B) | | Acid generator (A) | | Acid diffusion controller (C) | | Solvent (D) | |
| --- | --- | --- | --- | --- | --- | --- | --- | --- |
|  | Type | Amount (parts) | Type | Amount (parts) | Type | Amount (parts) | Type | Amount (parts) |
| Example 1 | B-1 | 100 | A-1 | 27 | C-1 | 2 | D-1 | 1400 |
|  |  |  |  |  |  |  | D-2 | 3300 |
| Example 2 | B-1 | 100 | A-2 | 27 | C-1 | 2 | D-1 | 1400 |
|  |  |  |  |  |  |  | D-2 | 3300 |
| Example 3 | B-1 | 100 | A-3 | 27 | C-1 | 2 | D-1 | 1400 |
|  |  |  |  |  |  |  | D-2 | 3300 |
| Example 4 | B-1 | 100 | A-2 | 27 | C-2 | 2 | D-1 | 1400 |
|  |  |  |  |  |  |  | D-2 | 3300 |
| Example 5 | B-1 | 100 | A-1 | 27 | C-1 | 2 | D-1 | 3300 |
|  |  |  |  |  |  |  | D-2 | 1400 |
| Example 6 | B-2 | 100 | A-2 | 27 | C-2 | 2 | D-1 | 1400 |
|  |  |  |  |  |  |  | D-2 | 3300 |
| Example 7 | B-3 | 100 | A-5 | 27 | C-2 | 2 | D-1 | 1400 |
|  |  |  |  |  |  |  | D-2 | 3300 |
| Example 8 | B-3 | 100 | A-6 | 27 | C-2 | 2 | D-1 | 1400 |
|  |  |  |  |  |  |  | D-2 | 3300 |
| Example 9 | B-4 | 100 | A-6 | 27 | C-1 | 2 | D-2 | 3300 |
|  |  |  |  |  |  |  | D-3 | 1400 |
| Example 10 | B-1 | 100 | A-1 | 27 | C-3 | 2 | D-1 | 1400 |
|  |  |  |  |  |  |  | D-2 | 3300 |
| Example 11 | B-5 | 100 | A-1 | 7 | C-1 | 2 | D-2 | 2600 |
|  |  |  | A-7 | 7 |  |  | D-3 | 1300 |
| Example 12 | B-5 | 100 | A-6 | 7 | C-2 | 2 | D-2 | 2600 |
|  |  |  | A-7 | 7 |  |  | D-3 | 1300 |
| Comparative Example 1 | B-1 | 100 | A-4 | 27 | C-1 | 2 | D-1 | 1400 |
|  |  |  |  |  |  |  | D-2 | 3300 |
| Comparative Example 2 | B-1 | 100 | A-4 | 27 | C-1 | 2 | D-1 | 3300 |
|  |  |  |  |  |  |  | D-2 | 1400 |
| Comparative Example 3 | B-5 | 100 | A-7 | 14 | C-1 | 2 | D-2 | 2600 |
|  |  |  |  |  |  |  | D-3 | 1300 |

The details of the acid generator (A), the resin (B), the acid diffusion controller (C), and the solvent (D) shown in Table 1 are given below.
<Acid Generator (A)>
(A-1) to (A-7): compounds shown by the following formulas (A-1) to (A-7)
(A-1)
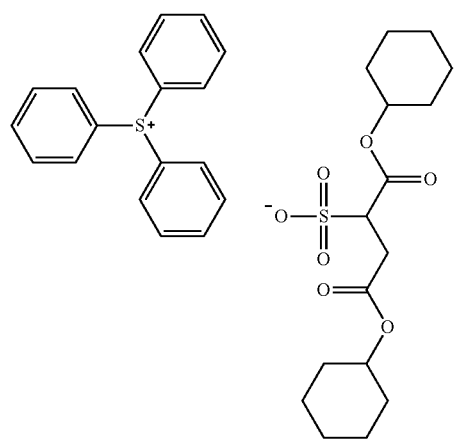
(A-2)
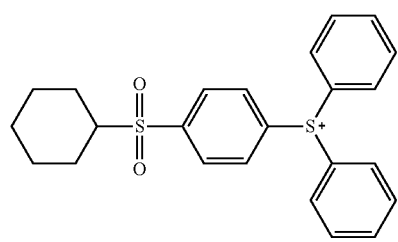
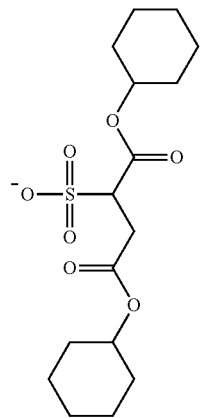
(A-3)
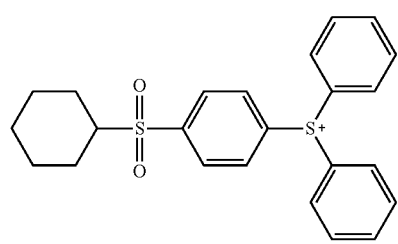
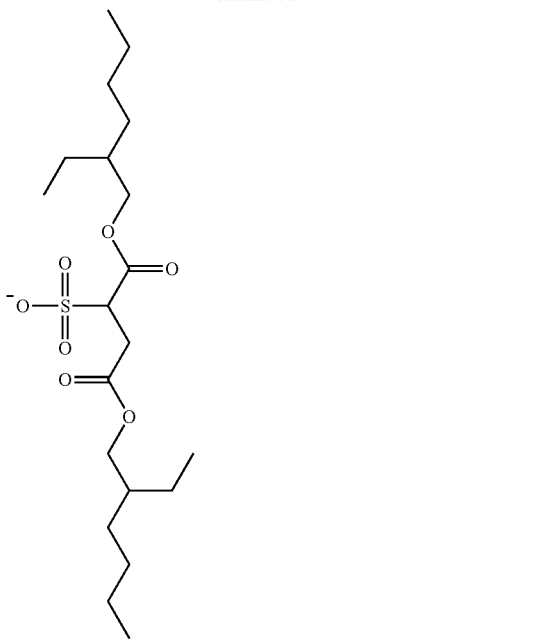
(A-4)
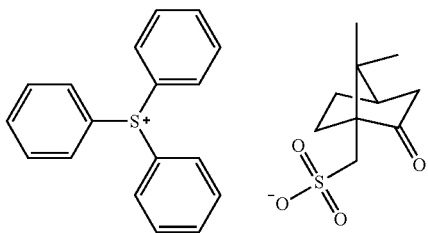
(A-5)
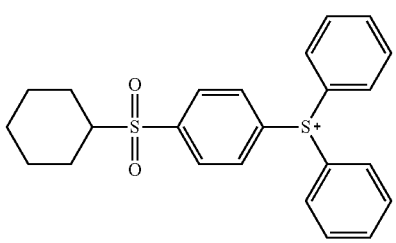
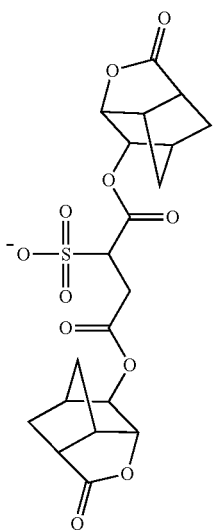

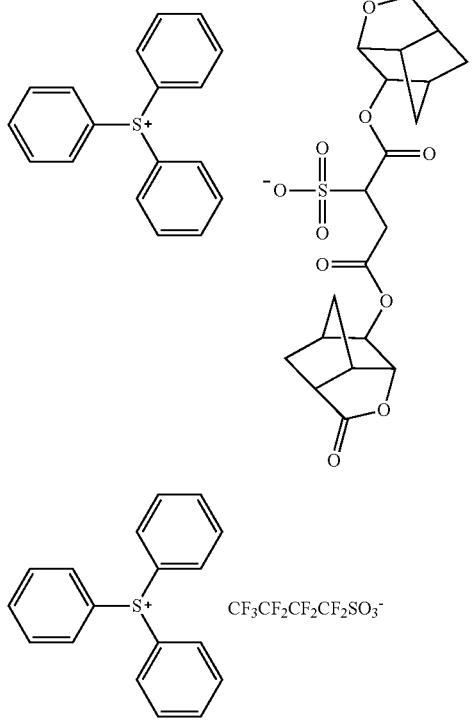

(A-6)

(A-7)

CF₃CF₂CF₂CF₂SO₃⁻

<Resin (B)>
(B-1): resin (B-1) obtained in Synthesis Example 1
(B-2): resin (B-2) obtained in Synthesis Example 2
(B-3): resin (B-3) obtained in Synthesis Example 3
(B-4): resin (B-4) obtained in Synthesis Example 4
(B-5): resin (B-5) obtained in Synthesis Example 5
<Acid Diffusion Controller (C)>
(C-1): tri-n-octylamine
(C-2): compound shown by the following formula (C-2)
(C-3): N-t-butoxycarbonyl-2-phenylbenzimidazole

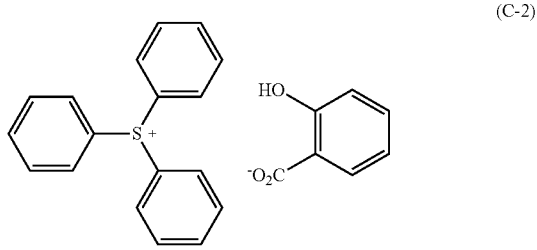

(C-2)

<Solvent (D)>
(D-1): ethyl lactate
(D-2): propylene glycol monomethyl ether acetate
(D-3): cyclohexanone

[3-1] Evaluation of Radiation-Sensitive Composition (EB Exposure)

The composition solution (radiation-sensitive compositions of Examples 1 to 10 and Comparative Example 1 and 2) was spin-coated onto a silicon wafer using a system "CLEAN TRACK ACT-8" (manufactured by Tokyo Electron, Ltd.), and pre-baked (PB) under the conditions shown in Table 2 to form a resist film having a thickness of 50 nm. The resist film was exposed to electron beams using an electron beam drawing system ("HL800D" manufactured by Hitachi, Ltd., output: 50 KeV, current density: 5.0 A/cm²). The resist film was then subjected to post-exposure bake (PEB) under the conditions shown in Table 2. The resist film subjected to PEB was developed at 23° C. for 1 minute by a puddle method using a 2.38% tetramethylammonium hydroxide aqueous solution, rinsed with purified water, and dried to obtain a resist pattern.

The resist pattern thus obtained was evaluated as described below. The evaluation results are shown in Table 2.

(3-1-1) Sensitivity (L/S)

A dose at which a line-and-space pattern (1L1S) including a line area (width: 130 nm) and a space area (groove) (width: 130 nm) defined by the adjacent line areas was formed at a 1:1 line width was determined to be an optimum dose, and the sensitivity was evaluated based on the optimum dose.

(3-1-2) Nano Edge Roughness (i)

Figure 2:
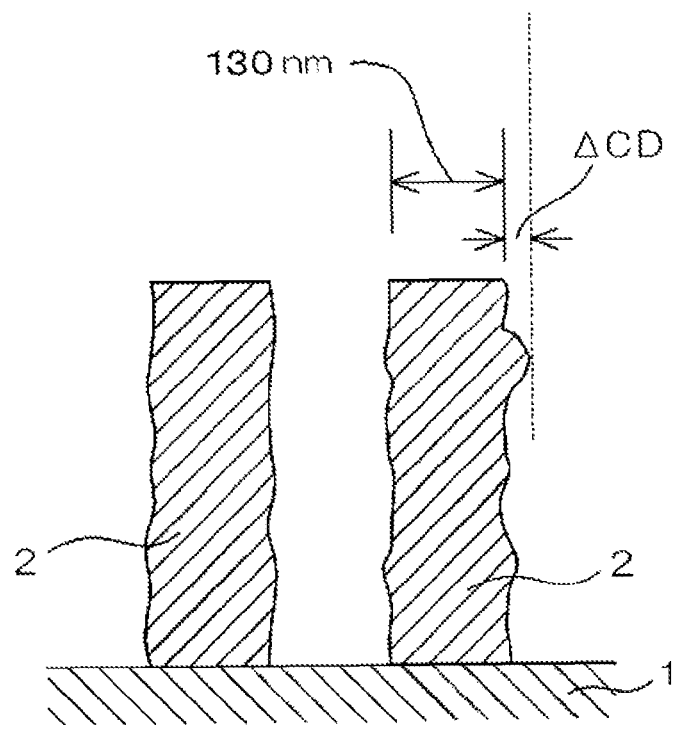
FIG. 2 is a cross-sectional view schematically showing the shape of a line pattern.

The line pattern of a line-and-space pattern (1L1S) (design line width: 130 nm) was observed using a scanning electron microscope ("S-9220" manufactured by Hitachi, Ltd.). The nano edge roughness was evaluated by determining the difference "ΔCD" between the design line width (130 nm) and the line width in an area where elevations and depressions significantly occurred along a side 2a of a line area 2 of a resist film formed on a silicon wafer 1 (see FIGS. 1 and 2) using a CD-scanning electron microscope (SEM) ("S-9220" manufactured by Hitachi High-Technologies Corporation). Note that elevations and depressions are exaggerated in FIGS. 1 and 2.

(3-1-3) Resolution (L/S)

The minimum line width (nm) of a line pattern of a line-and-space pattern (1L1S) that was resolved at the optimum dose was taken as the resolution.

[3-2] Evaluation of Radiation-Sensitive Composition (ArF Exposure)

A film (thickness: 75 nm) of the composition solution (radiation-sensitive compositions of Examples 11 and 12 and Comparative Example 3) was formed on a 12-inch silicon wafer on which an underlayer antireflective film ("ARC66" manufactured by Nissan Chemical Industries, Ltd.) was formed, and prebaked (PB) under the conditions shown in Table 3. The upperlayer film-forming composition disclosed in Example 1 of WO2008/047678 was spin-coated onto the film, and prebaked (PB) (90° C., 60 sec) to form a film having a thickness of 90 nm. The film was subjected to reduced projection exposure via a mask pattern using an ArF immersion scanner ("NSR S610C" manufactured by Nikon Corporation) (NA=1.3, ratio=0.800, Annular). The film was then subjected to PEB under the conditions shown in Table 3. The film subjected to PEB was developed using a 2.38 mass % tetramethylammonium hydroxide aqueous solution, rinsed with water, and dried to form a positive-tone resist pattern.

The resist pattern thus obtained was evaluated as described below. The evaluation results are shown in Table 3.

(3-2-1) Mask Error Enhancement Factor (MEEF)

A dose at which a line-and-space (LS) pattern having a line width of 50 nm was formed via exposure through a mask pattern (target size: 50 nm 1L/1S) under the above evaluation conditions was determined to be an optimum dose. An LS pattern (pitch: 100 nm) was formed at the optimum dose using a mask pattern (line width target size: 46 nm, 48 nm, 50 nm, 52 nm, or 54 nm), and the line width of the resist film was measured using a scanning electron microscope (SEM) ("CG4000" manufactured by Hitachi, Ltd.). A graph was drawn by plotting the target size (nm) (horizontal axis) and the line width (nm) of the resist film formed using each mask pattern (vertical axis), and the slope of the straight line of the graph was calculated as the mask error enhancement factor (MEEF).

The mask production cost can be reduced by reducing the MEEF.

(3-2-2) Nano Edge Roughness (II)

A dose at which a resist pattern having a line width of 50 nm was formed via exposure through a mask pattern (target size: 50 nm 1L/1.8S) under the above evaluation conditions was determined to be an optimum dose. The line width of a 50 nm 1L/1.8S pattern obtained at the optimum dose was observed from above at an arbitrary ten points using a scanning electron microscope (SEM) ("CG4000" manufactured by Hitachi, Ltd.), and a variation (3 sigma) in line width was taken as the LWR.

A small LWR indicates that the pattern has excellent linearity.

(3-2-3) Minimum Collapse Dimension

The resist film was exposed through a mask pattern (target size: 50 nm 1L/1.8S) under the above evaluation conditions while changing the dose by 1 mJ. The line width of the pattern formed at a dose lower by 1 mJ than the dose at which line collapse occurred was taken as the minimum collapse dimension (measured using a scanning electron microscope (SEM) ("CG4000" manufactured by Hitachi, Ltd.)).

A small minimum collapse dimension indicates that the pattern has excellent collapse resistance.

pattern, as compared with the radiation-sensitive compositions of Comparative Examples 2 and 3 that did not include any of the acid generators (A-1) to (A-3), (A-5), and (A-6).

While the acid generator (A-4) exhibited poor solubility in a solvent (i.e., an appropriate solvent must be selected), the acid generators (A-1) to (A-3), (A-5), and (A-6) exhibited excellent solubility in a solvent.

The radiation-sensitive composition and a compound according to the embodiment of the invention may be used for photolithography employed in the production of semiconductor devices (e.g., IC), liquid crystal devices, circuit boards (e.g., thermal head), and the like. More specifically, the radiation-sensitive composition according to the embodiment of the invention may suitably be used for photolithography that utilizes an exposure light source having a wavelength of 220 nm or less (e.g., deep ultraviolet rays (e.g., ArF excimer laser light) or electron beams), and the compound according to the embodiment of the invention may be suitable as an acid generator included in the radiation-sensitive composition.

Since the radiation-sensitive composition according to the embodiments of the invention exhibits high resolution when forming a line-and-space resist pattern and shows only a small degree of nano edge roughness, the radiation-sensitive composition may be useful for forming a fine pattern using EB, EUV, or X-rays. Therefore, the radiation-sensitive composition may be useful as a material for forming a chemically-

TABLE 2

|  | PB conditions | | PEB conditions | | Sensitivity | Nano edge | Resolution |
|---|---|---|---|---|---|---|---|
|  | Temp. (° C.) | Time (s) | Temp. (° C.) | Time (s) | (μC/cm$^2$) | roughness (i) (nm) | (nm) |
| Example 1 | 110 | 60 | 100 | 60 | 42.0 | 11 | 70 |
| Example 2 | 110 | 60 | 100 | 60 | 43.0 | 9 | 70 |
| Example 3 | 110 | 60 | 100 | 60 | 42.0 | 10 | 70 |
| Example 4 | 110 | 60 | 100 | 60 | 40.0 | 9 | 60 |
| Example 5 | 110 | 60 | 100 | 60 | 42.0 | 11 | 70 |
| Example 6 | 110 | 60 | 100 | 60 | 39.0 | 9 | 60 |
| Example 7 | 110 | 60 | 140 | 60 | 37.0 | 9 | 60 |
| Example 8 | 110 | 60 | 140 | 60 | 36.0 | 9 | 70 |
| Example 9 | 110 | 60 | 140 | 60 | 37.0 | 9 | 60 |
| Example 10 | 110 | 60 | 100 | 60 | 41.0 | 11 | 70 |
| Comparative Example 1 | Could not be evaluated (i.e., the acid generator (A) was not dissolved in the solvent (D)) | | | | | | |
| Comparative Example 2 | 110 | 60 | 100 | 60 | 50.0 | 16 | 90 |

TABLE 3

|  | PB conditions | | PEB conditions | | MEEF | Nano edge roughness (ii) (nm) | Minimum collapse dimension (nm) |
|---|---|---|---|---|---|---|---|
|  | Temp. (° C.) | Time (s) | Temp. (° C.) | Time (s) | | | |
| Example 11 | 110 | 60 | 100 | 60 | 3.4 | 5 | 35 |
| Example 12 | 110 | 60 | 100 | 60 | 3.5 | 5 | 34 |
| Comparative Example 3 | 110 | 60 | 100 | 60 | 4.0 | 6 | 44 |

As is clear from Tables 2 and 3, it was confirmed that the radiation-sensitive compositions of Examples 1 to 12 including any of the acid generators (A-1) to (A-3), (A-5), and (A-6) could produce a chemically-amplified positive-tone resist film that effectively responds to electron beams or extreme ultraviolet rays, shows only a small degree of roughness and excellent resolution, and accurately and stably produces a fine amplified resist for producing semiconductor devices that are expected to be further miniaturized in the future.

Obviously, numerous modifications and variations of the present invention are possible in light of the above teachings. It is therefore to be understood that within the scope of the appended claims, the invention may be practiced otherwise than as specifically described herein.

The invention claimed is:

1. A radiation-sensitive composition comprising:
a photoacid generator shown by formula (1),

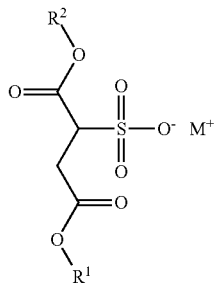

(1)

wherein each of $R^1$ and $R^2$ individually represents
- (a1) a substituted or unsubstituted linear or branched monovalent hydrocarbon group having 1 to 30 carbon atoms,
- (a2) the hydrocarbon group as defined in (a1) which further includes at least one of an ester bond, an amide bond, a urethane bond, and a sulfide bond,
- (a3) a substituted or unsubstituted cyclic or cyclic structure-containing monovalent hydrocarbon group having 3 to 30 carbon atoms,
- (a4) the hydrocarbon group as defined in (a3) which further includes at least one of an ester bond, an amide bond, a urethane bond, and a sulfide bond,
- (a5) a substituted or unsubstituted aryl group having 6 to 30 carbon atoms, or
- (a6) a substituted or unsubstituted cyclic organic group having 4 to 30 carbon atoms and optionally having a monovalent heteroatom, and $M^+$ represents a monovalent caution.

2. The radiation-sensitive composition according to claim 1, wherein the monovalent onium cation represented by $M^+$ is a sulfonium cation shown by formula (2) or an iodonium cation shown by formula (3),

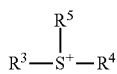

(2)

wherein each of $R^3$, $R^4$, and $R^5$ individually represents a substituted or unsubstituted linear or branched alkyl group having 1 to 10 carbon atoms or a substituted or unsubstituted aryl group having 6 to 18 carbon atoms, or two of $R^3$, $R^4$, and $R^5$ bond to each other to form a cyclic structure together with the sulfur atom in formula (2), and the remainder of $R^3$, $R^4$, and $R^5$ represents a substituted or unsubstituted linear or branched alkyl group having 1 to 10 carbon atoms or a substituted or unsubstituted aryl group having 6 to 18 carbon atoms,

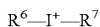 (3)

wherein each of $R^6$ and $R^7$ individually represents a substituted or unsubstituted linear or branched alkyl group having 1 to 10 carbon atoms or a substituted or unsubstituted aryl group having 6 to 18 carbon atoms, or bond to each other to form a cyclic structure with the iodine atom in formula (3).

3. The radiation-sensitive composition according to claim 1, further comprising a resin which comprises at least one repeating unit among repeating units shown by formulas (b-1) to (b-5),

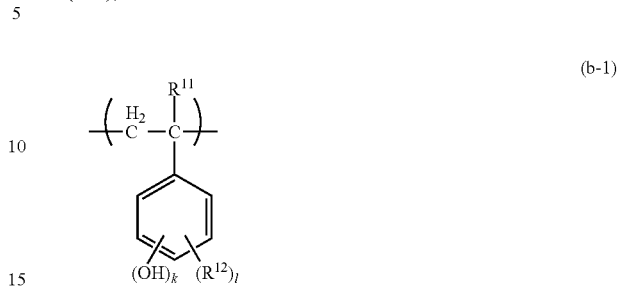

(b-1)

wherein $R^{11}$ represents a hydrogen atom or a methyl group, $R^{12}$ represents a linear or branched alkyl group having 1 to 12 carbon atoms or a linear or branched alkoxy group having 1 to 12 carbon atoms, k is an integer from 0 to 3, and l is an integer from 0 to 3, wherein $k+l \leq 5$ is satisfied,

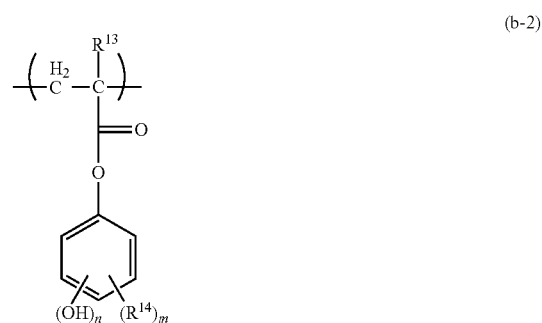

(b-2)

wherein $R^{13}$ represents a hydrogen atom or a methyl group, $R^{14}$ represents a linear or branched alkyl group having 1 to 12 carbon atoms or a linear or branched alkoxy group having 1 to 12 carbon atoms, m is an integer from 0 to 3, and n is an integer from 0 to 3, wherein $m+n \leq 5$ is satisfied,

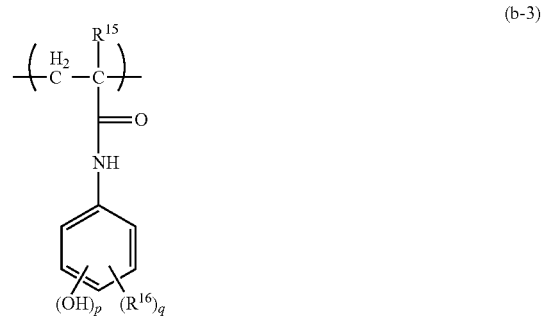

(b-3)

wherein $R^{15}$ represents a hydrogen atom or a methyl group, $R^{16}$ represents a linear or branched alkyl group having 1 to 12 carbon atoms or a linear or branched alkoxy group having 1 to 12 carbon atoms, p is an integer from 0 to 3, and q is an integer from 0 to 3, wherein $p+q \leq 5$ is satisfied,

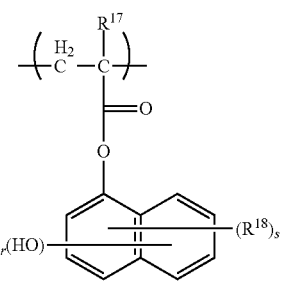

(b-4)

wherein $R^{17}$ represents a hydrogen atom or a methyl group, $R^{18}$ represents a linear or branched alkyl group having 1 to 12 carbon atoms or a linear or branched alkoxy group having 1 to 12 carbon atoms, r is an integer from 0 to 3, and s is an integer from 0 to 3, where p+q≤5 is satisfied,

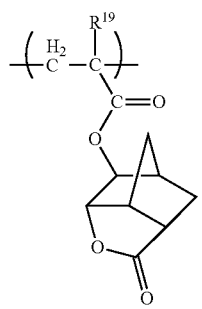

(b-5)

wherein $R^{19}$ represents a hydrogen atom or a methyl group.

4. The radiation-sensitive composition according to claim 1, further comprising at least one compound of ethylene glycol monoalkyl ether acetate and propylene glycol monoalkyl ether acetate as a solvent in an amount of 70 to 100 parts by mass based on 100 parts by mass of the solvent in total.

5. A compound shown by formula (1),

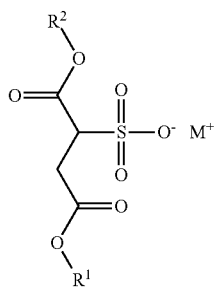

(1)

wherein each of $R^1$ and $R^2$ individually represents (a1) a substituted or unsubstituted linear or branched monovalent hydrocarbon group having 1 to 30 carbon atoms, (a2) the hydrocarbon group as defined in (a1) which further includes at least one of an ester bond, an amide bond, a urethane bond, and a sulfide bond, (a3) a substituted or unsubstituted cyclic or cyclic structure-containing monovalent hydrocarbon group having 3 to 30 carbon atoms, (a4) the hydrocarbon group as defined in (a3) which further includes at least one of an ester bond, an amide bond, a urethane bond, and a sulfide bond, (a5) a substituted or unsubstituted aryl group having 6 to 30 carbon atoms, or (a6) a substituted or unsubstituted cyclic organic group having 4 to 30 carbon atoms and optionally having a monovalent heteroatom, and $M^+$ represents a monovalent onium cation, the monovalent onium cation represented by $M^+$ being a sulfonium cation shown by formula (2) or an iodonium cation shown by formula (3),

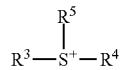

(2)

wherein each of $R^3$, $R^4$, and $R^5$ individually represents a substituted or unsubstituted linear or branched alkyl group having 1 to 10 carbon atoms or a substituted or unsubstituted aryl group having 6 to 18 carbon atoms, or two of $R^3$, $R^4$, and $R^5$ bond to each other to form a cyclic structure together with the sulfur atom in formula (2), and the remainder of $R^3$, $R^4$, and $R^5$ represents a substituted or unsubstituted linear or branched alkyl group having 1 to 10 carbon atoms or a substituted or unsubstituted aryl group having 6 to 18 carbon atoms, $$R^6—I^+—R^7 \quad (3)$$

wherein each of $R^6$ and $R^7$ individually represents a substituted or unsubstituted linear or branched alkyl group having 1 to 10 carbon atoms or a substituted or unsubstituted aryl group having 6 to 18 carbon atoms, or bond to each other to form a cyclic structure with the iodine atom in formula (3).

6. The radiation-sensitive composition according to claim 1, further comprising an acid diffusion controller.

7. The radiation-sensitive composition according to claim 6, wherein the acid diffusion controller comprises a nitrogen-containing organic compound, a photosensitive basic compound, or both thereof.

8. The radiation-sensitive composition according to claim 1, further comprising an additional photoacid generator other than the acid generator shown by formula (1).

9. The radiation-sensitive composition according to claim 8, wherein an amount of the additional photoacid generator is 80 parts by mass or less based on 100 parts by mass of the acid generator shown by formula (1).

10. The radiation-sensitive composition according to claim 8, wherein an amount of the additional photoacid generator is 50 parts by mass or less based on 100 parts by mass of the acid generator shown by formula (1).

* * * * *